United States Patent [19]

Cullinan et al.

[11] 4,203,898

[45] May 20, 1980

[54] AMIDE DERIVATIVES OF VLB, LEUROSIDINE, LEUROCRISTINE AND RELATED DIMERIC ALKALOIDS

[75] Inventors: George J. Cullinan, Trafalger; Koert Gerzon, Indianapolis, both of Ind.

[73] Assignee: Eli Lilly and Company, Indianapolis, Ind.

[21] Appl. No.: 954,514

[22] Filed: Oct. 25, 1978

Related U.S. Application Data

[63] Continuation of Ser. No. 828,693, Aug. 29, 1977, abandoned, which is a continuation-in-part of Ser. No. 721,650, Sep. 8, 1976, abandoned, which is a continuation-in-part of Ser. No. 539,681, Jan. 9, 1975, abandoned, which is a continuation-in-part of Ser. No. 446,869, Feb. 28, 1974, abandoned, which is a continuation-in-part of Ser. No. 347,275, Apr. 2, 1973, abandoned.

[51] Int. Cl.² .......................................... C07D 519/04
[52] U.S. Cl. ................................ 260/244.4; 424/258; 424/262
[58] Field of Search .................................. 260/244.4

[56] References Cited

U.S. PATENT DOCUMENTS

| 3,954,773 | 5/1976 | Neuss et al. ...................... 260/244.4 |
| 4,115,388 | 9/1978 | Thompson et al. ............... 260/244.4 |

FOREIGN PATENT DOCUMENTS 813168 12/1974 Belgium .

Primary Examiner—Donald G. Daus
Assistant Examiner—David E. Wheeler
Attorney, Agent, or Firm—James L. Rowe; Arthur R. Whale

[57] ABSTRACT

Amide derivatives of VLB, leurosidine, leurocristine and related dimeric alkaloids are useful as anti viral and anti-neoplastic agents or as intermediates in the preparation of such agents.

23 Claims, No Drawings

AMIDE DERIVATIVES OF VLB, LEUROSIDINE, LEUROCRISTINE AND RELATED DIMERIC ALKALOIDS

CROSS-REFERENCE

This application is a continuation of our application Ser. No. 828,693, filed Aug. 29, 1977, now abandoned which was a continuation-in-part of application Ser. No. 721,650 filed Sept. 8, 1976, now abandoned, which was a continuation-in-part of Ser. No. 539,681, filed Jan. 9, 1975, now abandoned, which was a continuation-in-part of application Ser. No. 446,869 filed Feb. 28, 1974, now abandoned, which was a continuation-in-part of application Ser. No. 347,275, filed Apr. 2, 1973, now abandoned.

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincristine) (both in U.S. Pat. No. 3,205,220), deoxy VLB "A" and "B", *Tetrahedron Letters*, 783 (1958) (desacetyl leurosine hydrazine is also disclosed therein); 4-desacetoxy vinblastine (U.S. Pat. No. 3,954,773; 4-desacetoxy-3'-hydroxyvinblastine (U.S. Pat. No. 3,944,554; leurocolombine (U.S. Pat. No. 3,890,325) and vincadioline (U.S. Pat. No. 3,887,565). Two of these alkaloids, VLB and leurocristine, are now marketed as drugs for the treatment of malignancies, particularly the leukemias and related diseases in humans. Of these marketed compounds, leurocristine is a most active and useful agent in the treatment of leukemias but is also the least abundant of the anti-neoplastic alkaloids of *Vinca rosea*.

Chemical modification of the Vinca alkaloids has been rather limited. In the first place, the molecular structures involved are extremely complex and chemical reactions which affect a specific function of the molecule are difficult to develop. Secondly, alkaloids lacking desirable chemo-therapeutic properties have been recovered from *Vinca rosea* fractions, and a determination of their structures has led to the conclusion that these compounds are closely related to the active alkaloids. Thus, antineoplastic activity seems to be limited to very specific structures, and the chances of obtaining more active drugs by modification of these structures would seem to be correspondingly slight. Among the successful modifications of physiologically-active alkaloids has been the preparation of dihydro VLB (U.S. Pat. No. 3,352,868) and the replacement of the acetyl group at C-4 (carbon no. 4 of the VLB ring system-see the numbered structure below) with higher alkanoyl group or with unrelated acyl groups. (See U.S. Pat. No. 3,392,173.) Several of these derivatives are capable of prolonging the life of mice inoculated with P1534 leukemia. One of the derivatives in which a chloracetyl group replaced the C-4 acetyl group of VLB was also a useful intermediate for the preparation of structurally modified VLB compounds in which an N,N-dialkylglycl group replaced the C-4 acetyl group of VLB (see U.S. Pat. No. 3,387,001). An intermediate compound, namely 4-desacetyl VLB, was produced during the chemical reactions leading to these latter derivatives. This intermediate, in which the C-4 acyl group was lacking, leaving an unesterified hydroxy group, has been reported to be a toxic material having little in vivo chemotherapeutic activity against the P1534 murine leukemia system by Hargrove, *Lloydia*, 27, 340 (1964).

SUMMARY OF THE INVENTION

This invention provides a group of compounds represented by Formula I below:

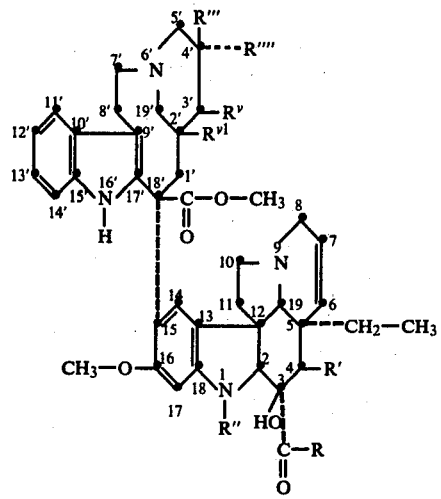

wherein R is $NH_2$, $NH-NH_2$, $N(CH_3)_2$, $N_3$, $NH-CH_2-Y$ wherein Y is H, CN, CHO, COOH, $C\equiv CH$, $CH(O-C_1-C_3\text{-alkyl})_2$, $COO-C_1-C_3$-alkyl, $CO-NH_2$ or

wherein Z is Cl, Br, OH, $C_1-C_3$-alkyl or $O-C_1-C_3$-alkyl, $NH-C_2-C_6$-alkyl$-X$, $NH-C_2-C_6$-alkyl$-(OH)_{1-3}$, $NH-(CH_2)_n-OAc$, $NH-(CH_2)_n-OCH_3$

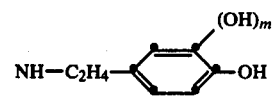

wherein m is 0 or 1, n is 2 or 3, X is $SY'$, $NH_2$, $NHCH_3$, $N(CH_3)_2$, NHAc, CN, H, phenyl, COOH, $COO-C_1-C_3$-alkyl or $CO-NH_2$, Y' is H, $C_1-C_3$-alkyl or a bond, said bond joining two sulfur atoms in two moieties of the above formula (I) where R is $NH-C_2-C_6$-alkyl X, X is SY' and Y' is a bond, and Ac is $C_1-C_{17}$-alkyl$-CO$ or $C_2-C_7$-alkenyl$-CO$, pyrrolidinyl or $NH-C_3-C_8$-cycloalkyl; R' is H, OH, $O-(C_1-C_3)$-alkanoyl or O-chloro-$(C_1-C_3)$-alkanoyl, R'' is hydrogen, $(C_1-C_3)$-alkyl or formyl, one of R''' and R'''' is hydrogen or hydroxyl and the other is ethyl, and $R^v$ and $R^{vl}$ are hydrogen or hydroxyl, with the proviso that, when either R''' or R'''' is hydrogen, $R^v$ and $R^{vl}$ must also be hydrogen.

In the above formula, when Y' is a bond, the compound which is intended to be represented is a disulfide produced by oxidation of two moles of a dimeric indoledihydroindole alkaloid C-3 carboxamide in which the amide group, R, is NH—$C_2$-$C_6$ alkyl—SH. In the resulting disulfide, the grouping R—R can be represented as NH—$C_2$-$C_6$alkyl-S—S—$C_2$-$C_6$alkyl—NH as in the cysteine-cystine couple.

A preferred group of amides of this invention are those according to the above formula including but not limited to amides of vinblastine, vincadioline, leurocristine, deoxy VLB "A" and "B", 4-desacetoxyvinblastine, 3'-hydroxy-4-desacetoxyvinblastine, leurosidine and the 4-desacetyl derivatives of the above dimeric alkaloids having a C-4 acetoxy group. Also included within the scope of this invention are the pharmaceutically-acceptable salts of the above bases, formed with nontoxic acids.

A particularly valuable group of compounds coming within the scope of this invention is represented by Formula II below:

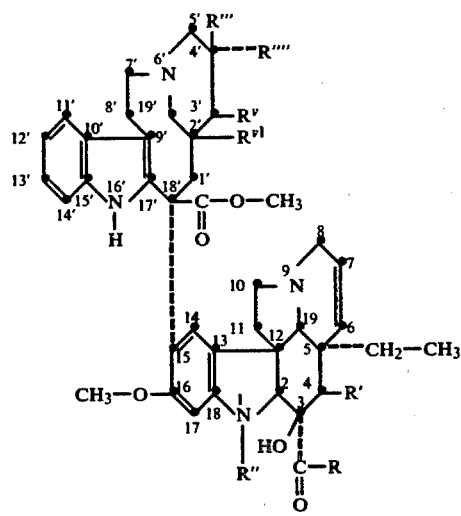

II wherein R is $NH_2$, NH—$NH_2$, $NHCH_3$, $N(CH_3)_2$, pyrrolidinyl, NH—alk—X, NH—($C_3$-$C_8$)-cycloalk, NH—alk—Am, NH—alk—(OH)$_{1-3}$, or $N_3$; wherein alk is ($C_2$-$C_6$) alkyl, Am is $NH_2$, $NHCH_3$ or $N(CH_3)_2$ and X is hydrogen, cyano, phenyl, carboxyl, carbo ($C_1$-$C_3$) alkoxy or carboxamide; wherein R' is H, OH, O—($C_1$-$C_3$)-alkanoyl or O-chloro-($C_1$-$C_3$)-alkanoyl; wherein R" is hydrogen, ($C_1$-$C_3$) alkyl or formyl; and wherein one of R''' and R'''' is hydrogen or hydroxyl and the other is ethyl, and $R^v$ and $R^{vI}$ are H or OH with the proviso that, if one of R''' or R'''' is hydrogen, $R^v$ and $R^{vI}$ must also be hydrogen.

Amides of the above formula in which R', R", R''', R'''', $R^v$ and $R^{vI}$ are defined as above and R is NH—alk—SH, NH—alk—S—S—alk—NH, or NH—alk—OH, particularly when alk is —$C_2H_4$— are extremely valuable compounds.

Amides of leurosidine, vincristine and VLB and related structures constitute a particularly useful subgroup among the compounds of Formula II and this subgroup is set forth in Formula III:

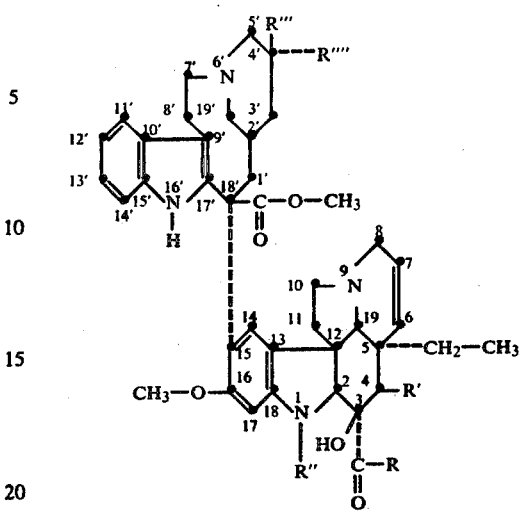

III wherein R is $NH_2$, NH—$NH_2$, $N(CH_3)_2$, NH—alk—X, $NH(C_3$-$C_8)$-cycloalk, NH—alk—Am, NH—alk—(OH)$_{1-3}$, or $N_3$; wherein alk is ($C_1$-$C_6$) alkyl, Am is $NH_2$, $NHCH_3$ or $N(CH_3)_2$ and X is hydrogen, cyano, phenyl, carboxyl, carbo ($C_1$-$C_3$) alkoxy or carboxamide; wherein R' is OH, O—($C_1$-$C_3$)-alkanoyl or O-chloro-($C_1$-$C_3$)-alkanoyl; wherein R" is hydrogen, ($C_1$-$C_3$) alkyl, formyl or ($C_1$-$C_3$)-alkanoyl; and wherein one of R''' and R'''' is hydroxyl and the other is ethyl.

Mercapto or hydroxy alkyl amides of the above formula (R is NH—alk—OH or NH—alk—SH) are also particularly useful as anti-tumor agents, as are the bis disulfides (NH—alk—S)$_2$ derived by oxidation from the corresponding mercaptoalkylamide (NH—alk—SH).

Within the subgroup represented by Formula III, the compounds represented by Formula IV, the simple amides of VLB and vincristine represent a preferred group, as do the 2-hydroxyethyl and the 2-mercaptoethylamides thereof.

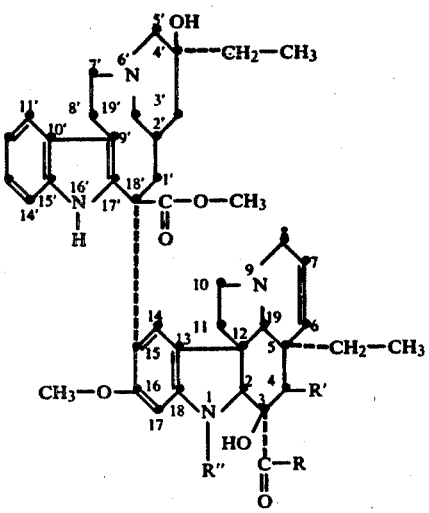

IV wherein R is $NH_2$; NH—$C_1$-$C_3$-alkyl or NH—$NH_2$, R' is OH, O—$C_1$-$C_3$ alkanoyl or O-Chloro-$C_1$-$C_3$ alkanoyl and R" is H, $C_1$-$C_3$ alkyl or lower alkanoyl.

Illustrative of $C_2$-$C_6$-alkyl-(OH)$_{1-3}$ and $C_2$-$C_6$-alkyl-X in the above formulas are the following: ethyl, 2-methylpentyl, isohexyl, isopentyl, n-pentyl, n-hexyl, sec-hexyl, isopropyl, n-butyl, sec-butyl, cyanopentyl, cyanoethyl, 2-hydroxy-n-hexyl, 5-cyano-n-pentyl, 2-hydroxyethyl, 2-acetoxyethyl, 3-hydroxypropyl, 2-dimethylaminoethyl, 2-aminoethyl, 2-methylaminoethyl, 2-hydroxypropyl, phenethyl, 4-phenylbutyl, 2-aminopropyl, 2-aminohexyl, 2-dimethylaminopropyl, 2,3-dihydroxypropyl, 2,2'-dihydroxyisopropyl, 2,2'-dihydroxy-t-butyl, 2,2',2''-trihydroxy-t-butyl, and the like. Similarly, the term $NH-C_2-C_6$-alkyl-SY' includes these radicals: β-mercaptoethyl, its disulfide, β-mercaptopropyl, its disulfide β-methylmercaptoethyl, β-propylmercaptopropyl and the like.

Illustrative of Y when it is

in the above formulas are the following radicals: phenyl, p-hydroxyphenyl, p-anisyl, p-tolyl, p-ethylphenyl, p-ethoxyphenyl, p-chlorophenyl; p-n-propylphenyl, p-cumyl, and the like. Thus, $NH-CH_2-Y$ can be β,β-dimethoxyethylamino, benzylamino, p-methylbenzylamino, p-chlorobenzylamino, glycylamide, N-glycyl, N-glycylethyl ester, formylmethylamino, β,β-diethoxyethylamino, cyanomethylamino and the like.

In the above formula, the terms "$(C_1-C_3)$-alkanoyl" and "chloro-$(C_1-C_3)$-alkanoyl" include groups such as acetyl, chloroacetyl, propionyl, 2-chloropropionyl, 2-chlorobutyryl and butyryl, these terms being represented by the formula $(C_1-C_3)$-alkyl-CO, an alkanoyl group, or by the formula $(C_1-C_3)$-alkyl (Cl)-CO, a chloroalkanoyl group. The term "$NH-(C_3-C_8)$-cycloalkyl" includes the radicals cyclopropylamino, cyclobutylamino, cyclopentylamino, cyclohexylamino, cycloheptylamino, and cyclooctylamino. The term "carbo-$(C_1-C_3)$-alkoxy" include the radicals carbomethoxy, carboethoxy, carboisopropoxy and carbo-n-propoxy.

The term "$C_1-C_3$ alkyl" as employed hereinabove includes the methyl, ethyl, n-propyl and iso-propyl groups. The term "$C_1-C_{17}$-alkyl-CO" means as alkanoyl group derived from alkanoic acids having from 2–18 carbon atoms; i.e., acetyl, propionyl, isobutyryl, stearyl, palmitoyl, lauryl, myristoyl, caproyl ($C_6$), isovaleroyl, capryloyl ($C_8$), capryl ($C_{10}$) and the like. The term "$C_2-C_7$-alkenyl-CO" means an unsaturated acid group having from 3 to 8 carbons; i.e., acrylyl, crotonyl, methacrylyl, allylacetyl, vinylacetyl, tiglyl, 2-methyl-2-hexenoyl, 2-octenoyl and the like.

When "X" in the radical "alk-X" is phenyl, the phenyl group can contain the standard aromatic substituents including lower alkyl, lower alkoxy, hydroxy, halo, nitro and the like and a given phenyl group can contain more than one of the above substituents, either the same or different. Examples of such groups are 4-hydroxyphenyl, 2,4-dichlorophenyl, 2-methyl-4-chlorophenyl, 2,4-dinitrophenyl, 3,5-xylyl, 4-tolyl, 2-tolyl, 3-ethoxyphenyl and the like.

Illustrative groups which are the nitrogen containing moiety of the $C_3$-carboxamido group in the various modified dimeric indole-dihydroindole alkaloids represented by the above formula include:

amide, methylamide, dimethylamide, ethylamide, n-butylamide, isohexylamide, 3-hydroxypropylamide, 2-hydroxy-n-hexylamide, 2-hydroxy-3-methylpentylamide, 2,2-dimethyl-2-hydroxyethylamide, acetaldehydeamide, diethyl acetalamide, 2-ethoxyethylamide, 2-methoxypropylamide, 2-acetoxyethylamide, 2-methacrylylethylamide, 2-myristylethylamide, 3-caprylpropylamide, cyanomethylamide, 2-cyanoethylamide, 3-cyano-n-propylamide, cyclopropylamide, cyclobutylamide, cyclooctylamide, 2-methylcyclobutylamide, p-hydroxybenzylamide, phenethylamide, 2-(m-methoxyphenyl)-2-methylethylamide, p-ethylbenzylamide, p-isopropoxybenzylamide, glycineamide, glycine ethylester amide, 2-carboxamido-ethylamide, 2-mercaptoethylamide and the bis disulfide produced by oxidation therefrom, 3-methylmercaptopropylamide, 2-n-propylmercaptopropylamide, 2-aminopropylamide, 4-amino-n-butylamide, 4-acetylamino-n-butylamide, and the like.

Non-toxic acids useful for forming pharmaceutically-acceptable acid addition salts of the amine bases include salts derived from inorganic acids such as: hydrochloric acid, nitric acid, phosphoric acid, sulfuric acid, hydrobromic acid, hydriodic acid, nitrous acid, phsophorus acid and the like, as well as salts of non-toxic organic acids including aliphatic mono and dicarboxylates, phenyl-substituted alkanoates, hydroxy alkanoates and alkandioates, aromatic acids, aliphatic and aromatic sulfonic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptaonate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

Compounds of the above formula can be described generically as either derivatives of VLB where R' is acetoxy, R'' is methyl, R''' is hydroxyl, R'''' is ethyl and $R^v$ and $R^{vl}$ are both H, or of desacetyl VLB where R'', R''', R'''', $R^v$ and $R^{vl}$ remain the same but R' is OH, or of leurocristine where R' is acetoxy, R'' is formyl, R''' is hydroxyl, R'''' is ethyl and both $R^v$ and $R^{vl}$ are H or of desacetyl leurocristine where R'', R''', R'''', $R^v$ and $R^{vl}$ remain the same but R' is hydroxy or as derivatives of desmethyl VLB (also known as desformylleurocristine) where R' is acetoxy, R'' is hydrogen, R''' and R'''' are hydroxyl and ethyl, respectively, and both $R^v$ and $R^{vl}$ are H, or of desacetyl desmethyl VLB (or desacetyl desformyl leurocristine) where R'', $R^v$ and $R^{vl}$ are hydrogen, R' is OH and R''' and R'''' are hydroxyl and ethyl, respectively, or of leurosidine where R' is acetoxy, R'' is methyl, R''' is ethyl, R'''' is hydroxyl and both $R^v$ and $R^{vl}$ are H, or of desmethyl leurosidine where R' is acetoxy, $R^v$ and $R^{vl}$ are hydrogen, R'' is hydroxyl and R''' and R'''' are ethyl and hydroxyl, respectively. In each instance, the term "desacetyl" refers to the lack of an acetyl group on the hydroxyl at C-4 of the complex indoledihydroindole ring system.

Other dimeric alkaloids, whose C-3 amide derivatives come within the scope of this invention include: Deoxy VLB "A" represented by the above formula when R is $CH_3O$, R' is acetoxy, R'' is methyl, R''', $R^v$ and $R^{vl}$ are H and R'''' is ethyl;

Deoxy VLB "B" wherein R, R', R", R$^v$ and R$^{v1}$ are the same but R'" is ethyl and R"" hydrogen. Both deoxy VLB isomers (also referred to as isoleurosine isomers) are fully disclosed in Neuss, Gorman, Cone and Huckstep, *Tetrahedron Letters*, 783 (1958);

Vincadioline, (3'-hydroxy VLB) an indole-dihydroindole having the following characteristics:

Melting point=218°-220.5° C. with decomposition;
X-ray powder diffraction pattern, using filtered chromium radiation; λ=2.2896° A.

| d in Å | I/I$_1$ |   | d in Å | I/I$_1$ |   |
|--------|---------|---|--------|---------|---|
| 11.40  | 10      |   | 4.17   | 10      |   |
| 9.55   | 100     | −1 | 3.99  | 60      |   |
| 8.87   | 90      | ⎫ | 3.71 20 |        |   |
|        |         | ⎬ −2 |      |         |   |
| 8.63   | 90      | ⎭ | 3.64   | 15      |   |
| 7.78   | 05      |   | 3.44   | 10      | B |
| 7.57   | 60      |   | 3.19   | 20      |   |
| 7.21   | 50      |   | 3.05   | 05      |   |
| 6.00   | 40      |   | 2.85   | 20      |   |
| 5.88   | 40      |   | 2.78   | 10      |   |
| 5.58   | 70      | −3 | 2.61  | 10      |   |
| 5.22   | 20      |   | 2.44   | 15      | B |
| 5.08   | 20      |   | 2.21   | 05      | B |
| 4.70   | 50      |   | 2.07   | 05      |   |
| 4.57   | 40      |   | 1.98   | 15      |   |
| 4.42   | 05      |   | 1.91   | 05      |   |
| 4.31   | 05      |   |        |         |   | nmr spectrum, δ at 7.13, 7.53, 8.04, 3.60, 6.61, 6.09, 3.79, 2.70, 9.77, 5.47, 2.09, 0.80, 5.85, 5.29, 5.63, 3.84, 0.91;

infra-red absorption maxima at 3480, 1745 and 1725 cm$^{-1}$;

molecular weight, 826;

Empirical formula, C$_{46}$H$_{58}$N$_4$O$_{10}$; and

Mass ions, m/e=826, 170, 371.

is prepared according to the following procedure: Leaves of plants containing crude vinca alkaloids; ie, *Catharanthus roseus* (*Vinca rosea*), are extracted with a water-immiscible solvent such as benzene. The benzene is distilled from the extract in the presence of aqueous tartaric acid. The pH of the resulting aqueous acidic extract is adjusted to pH=6 by the addition of base. Alternatively, the leaves are contacted with an aqueous acid at pH=3, and the resulting acidic layer extracted with benzene. The benzene layer is separated and discarded, and the pH of the aqueous layer adjusted to pH=6 as before. The dimeric alkaloids are then extracted from the aqueous layer into an organic solvent, customarily benzene. An optional gel exclusion filtration step can be carried out on the extracted alkaloids using a cross-linked dextran gel (sephadex G-25F), the mobile phase being a pH=3.0 0.1 M ammonium citrate buffer. A pressure of about 15 psi is employed during gel-exclusion chromatography. In this process, the dimeric alkaloid fraction containing leurocristine, VLB, des-N-methyl VLB, leuroformine, leurosine and leurosidine is eluted first. The dimeric alkaloids are extracted from the pH=3 buffer by adjusting the pH to 7.0 with base and then contacting the resulting aqueous solution with a water-immiscible solvent, preferably again benzene. Evaporation of the benzene yields a residue which can be dissolved in ethanol and leurosine crystallized directly therefrom. The leurosine crystals are separated by decantation, and the supernate thus obtained is acidified to pH=4.2 with 3 percent ethanolic sulfuric acid to convert the remaining dimeric alkaloids to their sulfate salts which precipitate. The precipitated salts are collected and are converted to the corresponding free alkaloidal bases by standard procedures as, for example, by dissolving the salts in water, adjusting the pH to 8.0 with ammonium hydroxide and extracting the dimeric alkaloids with a water-immiscible organic solvent, preferably methylenedichloride. Evaporation of the methylenedichloride yields the mixed dimeric alkaloids which are then chromatographed at high pressure over alumina (Activity III) using a ethyl acetate-methylenedichloride-water (25:75:0.4) solvent system as the eluant.

Operating pressures employed have been in the range 150–350 psi. As will be understood by those skilled in the art of high-pressure chromatography, equipment is available to carry out procedures at 4000–5000 psi and pressures in the range 7500–8000 psi appear feasible. Alkaloidal separation is in general more efficient at the higher pressures. High-pressure chromatography procedures are carried out in stainless steel equipment equipped with pressure resistant fittings.

The alkaloids are eluted in the following order in this chromatographic procedure: residual leurosine, VLB, des-N-methyl VLB, leurocristine and leurosidine. Identification of the dimeric alkaloid in the eluant fraction is carried out by standard procedures known to the art, as by thin layer chromatography.

After elution of the known alkaloids, there remain on the column several more polar dimeric alkaloids. These are eluted with methanol and rechromatographed until vincadioline is obtained as a separate fraction substantially free from other dimeric alkaloids present in the polar alkaloid fraction.

Leurocolombine, (2'-hydroxy VLB) having the following characteristics:

pKa's at 5.05, 6.3;

Infra-red absorption maxima at 2.80, 2.88, 3.35, 5.74, 6.18, 6.65, 6.83, 6.95, 7.25, 7.50, 8.11, 9.60, 9.90 and 10.75 microns;

Ultra-violet absorption maxima at 217 (a$_m$=51.091) and 265 (a$_m$=15,666) millimicrons;

Molecular weight, 826;

Empirical formula, C$_{46}$H$_{58}$N$_4$O$_{10}$;

Ion fragments by mass spectroscopy, m/e 795, 767, 749, 667, 649, 282, 170, 156, 154, 152, 144, 143;

proton nmr spectrum, chemical shifts in ppm at 751, 7.13, 0.90, 3.60, 3.75, 7.01, 3.84, 6.15, 5.29, 5.85, 5.48, 0.78, 2.68, 3.79, 2.70, 2.10 and 4.16; and forming a sulfate salt with the following x-ray powder diffraction pattern using filtered chromium radiation at 2.2896 Å.

| d in Å | I/I$_2$ |
|--------|---------|
| 17.00  | 30      |
| 12.50  | 100     |
| 9.45   | 50      |
| 7.70   | 10      |
| 7.20   | 60      |
| 6.20   | 20      |
| 5.70   | 30      |
| 4.95   | 05      |
| 4.65   | 20      |

Leurocolombine is prepared according to the following procedure: Leaves of plants containing crude vinca alkaloids; ie, *Catharanthus roseus* (*Vinca rosea*), are extracted with a water-immiscible solvent such as benzene. The benzene is distilled from the extract in the presence of aqueous tartaric acid. The pH of the resulting aqueous acidic extract is adjusted to pH=6 by the addition of base. Alternatively, the leaves are contacted with an aqueous acid at ph=3, and the resulting acidic layer extracted with benzene. The benzene layer is separated and discarded, and the pH of the aqueous layer adjusted to pH=6 as before. The dimeric alkaloids are then extracted from the aqueous layer into an organic solvent, customarily benzene. An optional gel exclusion filtration step can be carried out on the extracted alkaloids using a cross-linked dextran gel (sephadex G-25 F), the mobile phase being a pH=3.0, 0.1 M ammonium citrate buffer. A pressure of about 15 psi is employed during gel-exclusion chromatography. In this process, the dimeric alkaloid fraction containing leurocristine, VLB, des-N-methyl VLB, leuroformine, leurosine and leurosidine is eluted first. The dimeric alkaloids are extracted from the pH=3 buffer by adjusting the pH to pH=7.0 with base and then extracting the resulting aqueous solution with a water-immiscible solvent, preferably again benzene. Evaporation of the benzene yields a residue which can be dissolved in ethanol and leurosine crystallized directly therefrom. The leurosine crystals are separated by decantation, and the supernatant thus obtained is acidified to pH=4.2 with 3 percent ethanolic sulfuric acid to convert the remaining dimeric alkaloids to their sulfate salts which precipitate. The precipitated salts are collected and are converted to the corresponding free alkaloidal bases by standard procedures as, for example, by dissolving the salts in water, adjusting the pH≈8.0 with ammonium hydroxide and extracting the dimeric alkaloids with a water-immiscible organic solvent, preferably methylenedichloride. Evaporation of the methylenedichloride yields the mixed dimeric alkaloids which are then chromatographed at high pressure over alumina (Activity III-IV) using a ethyl acetate-methylenedichloride-water (25:75:0.4) solvent system as the eluant.

Operating pressures employed have been in the range 150–350 psi. As will be understood by those skilled in the art of high-pressure chromatography, equipment is available to carry out procedures at 4000–5000 psi an/-pressures in the range 7500–8000 psi appear feasible. Alkaloidal separation is in general more efficient at the higher pressures. High-pressure chromatography procedures are carried out in stainless steel equipment equipped with pressure resistant fittings.

The alkaloids are eluted in the following order in this chromatographic procedure: residual leurosine, VLB, leurocolombine, des-N-methyl VLB, leurocristine and leurosidine. Identification of leurocolombine and other dimeric alkaloids in the eluant fraction is carried out by standard procedures known to the art, as by thin layer chromatography.

4-Desacetoxyvinblastine, (psuedo VLB) has the following physical and chemical characteristics: melting point=183°–190° C. with decomposition after recrystallization from methanol; $[\alpha]_D^{26} = +95.3°$ (chloroform); molecular ion M+ =752, corresponding to an empirical formula $C_{44}H_{56}N_4O_7$.

Analysis Calcd. for $C_{44}H_{56}N_4O_7$—Analysis Calc.: C, 70.19; H, 7.50; N, 7.44; O, 14.87. Found: C, 69.71; H, 7.47; N, 7.08; O, 15.00.

4-Desacetoxyvinblastine prepared according to the following procedure: Leaves of plants containing crude vinca alkaloids; i.e., *Catharanthus roseus* (*Vinca rosea*), previously moistened with aqueous ammonia, are extracted with a water-immiscible solvent such as benzene. The benzene is distilled from the extract in the presence of aqueous tartaric acid. The tartaric acid layer is extracted with a water-immiscible organic solvent and is then made basic by the addition of ammonia. The dimeric alkaloids are then extracted from the alkaline layer into an organic solvent, customarily benzene. Evaporation of the benzene yields a mixture of amorphous dimeric alkaloids which are dissolved in benzene and chromatographed over alumina (CAMAG-Activity III).

The alkaloids are eluted in the following order: leurosine, VLB, des-N-methyl VLB, leurocristine and leurosidine. Identification of the dimeric alkaloids in the eluant fraction is carried out by standard procedures known to the art, as by thin layer chromatography. VLB is customarily eluted with a benzene-chloroform (1:1) solvent mixture. The procedure for obtaining the VLB fraction is more fully set forth in U.S. Pat. No. 3,225,030.

VLB fractions thus obtained were shown by thin layer chromatography to contain small quantities of a second alkaloid, layer identified as 4-desacetoxyvinblastine. This second alkaloid is isolated as follows: The VLB fraction is converted to the corresponding sulfate salts by standard procedure and the sulfates subjected to a gradient pH separation procedure in which the sulfates are dissolved in 2 percent aqueous citric acid, and the citric acid solution extracted twice with benzene. The pH is then raised to pH=5.5 by the addition of ammonia and two more benzene extractions are carried out. The second fraction is chromatographed over alumina (activity III). The chromatogram is developed with benzene. Fractions shown by thin layer chromatography to contain a second alkaloid in addition to VLB are combined and rechromatographed over alumina and the chromatogram again developed with benzene. This procedure is repeated. Fractions containing substantially only the second alkaloid, 4-desacetoxy VLB, with only minor amounts of VLB are combined and recrystallized from methanol. 4-Desacetoxy VLB thus recrystallized is then further purified by preparative TLC over silica using as eluant a 3:2:4 diethylamine-chloroform-benzene solvent mixture. 4-Desacetoxy-3'-hydroxyvinblastine with the following physical characteristics:

proton nmr spectrum peaks at δ4.075(5), 5.85(15), 5.46–5.78 (broad multiplet)

mass spectrum: ions at m/e 768, 411, 371, 224, 170, 102.

4-Desacetoxy-3'-hydroxyvinblastine is prepared according to the following procedure: Defatted leaves of plants containing crude vinca alkaloids; i.e., *Catharanthus roseus* (*Vinca rosea*), previously moistened with aqueous ammonia, are extracted with a water-immiscible solvent such as benzene. The benzene is distilled from the extract in the presence of aqueous tartaric acid. The tartaric acid layer is then made basic by the addition of ammonia. The dimeric alkaloids are extracted from the alkaline layer into an organic solvent, customarily benzene. Evaporation of the solvent yields a mixture of amorphous dimeric alkaloids. The dimeric alkaloid fraction is dissolved in ethanol and the corresponding sulfate salts formed by the addition of ethanolic sulfuric acid. The crystalline mixed sulfate salts are collected and then converted to the corresponding, free bases by solution in water, basifying the aqueous solution and extracting the alkaloids into a water-immiscible organic solvent, customarily methylene dichloride. Evaporation of the solvent yields a mixture of amorphous dimeric alkaloids which are redissolved in methylene dichloride and chromatographed over alumina (CAMAG-Activity III-IV).

The alkaloids are eluted in the following order: leurosine, VLB, des-N-methyl VLB, leurocristine and leurosidine. Identification of the dimeric alkaloids in the eluant fraction is carried out by standard procedures known to the art, as by thin layer chromatography. Chromatography was carried out in a stainless steel column, 5 cm. by 730 cm., at a pressure of 200–400 psi. The alumina-to-charge ratio was approximately 300 to 1. The eluate was monitored at 280 mµ, and fractions were separated based upon the peaks observed in the ultraviolet profile. Fractions were identified containing predominantly leurosine, vinblastine, des-N-methylvinblastine, and leurocristine by thin layer chromatography. Post des-N-methylvinblastine, preleurocristine fractions were accumulated, i.e., fractions containing more than one dimeric alkaloid occurring after the peak des-N-methylvinblastine fraction and prior to the peak leurocristine fraction, and were converted to the corresponding sulfate salts by treatment with an excess of 1 percent ethanolic sulfuric acid. The sulfate salts were subjected to a gradient pH separation procedure in which a solution of the sulfate salts in citric acid buffer at pH=3.4 was extracted with benzene. The pH of the citric acid solution was raised in increments of one-half pH unit, and the resulting aqueous layer extracted with benzene. 4-Desacetoxy-3'-hydroxyvinblastine was found to be present by thin layer chromatography in extracts at pH=5.4 and 5.9. Sulfates (VLB and leurocristine were shown by TLC to be the chief dimeric alkaloid impurities present), recovered from the pH=5.4 extract, were dissolved in 5 ml. of water and the acidity of the aqueous solution adjusted to pH=9 by the addition of ammonium acetate. The precipitated alkaloidal free bases were separated by centrifugation, dissolved in 3 ml. of methylenechloride and chromatographed at high pressure in a stainless steel 5/16" by 6 meter column packed with neutral alumina [Woelm N-18 (18–30µ)] using a linear gradient of 0–5 percent ethanol in methylene chloride. The column was operated at about 1100 psi with a consequent flow rate of 180 ml/hr. Fractions were collected every 3 minutes after material began to appear in the column effluent as determined by ultra-violet profile. Fractions 30–32 contained 4-desacetoxy-3'-hydroxylvinblastine, as shown by TLC on silica gel using an ether-diethylamine-toluene-methanol (100:5:5:5) solvent system.

Vincadioline is represented by the above formula when R is methoxy, R' is acetoxy, R" is methyl, R''' and $R^v$ are OH, R'''' is ethyl and $R^{vi}$ is H. Its preparation and properties are more fully disclosed in Cullinan and Jones, U.S. Pat. No. 3,887,565. Leurocolumbine is represented by the above formula when R is methoxy, R' is acetoxy, R" is methyl, R'''' and $R^{vi}$ are OH, R'''' is ethyl and $R^v$ is H. Its preparation and properties are more fully disclosed in Smith (Tafur) and Dorman, U.S. Pat. No. 3,890,325. 4-Desacetoxyvinblastine (psuedo VLB) is represented by the above formula when R is methoxy, R', $R^v$ and $R^{vi}$ are H, R" is methyl, R''' is OH and R'''' is ethyl. Its preparation and properties are more fully disclosed in Neuss and Barnes, U.S. Pat. No. 3,954,773. 3'-Hydroxy-4-desacetoxyvinblastine is more fully described in Tafur, U.S. Pat. No. 3,944,554.

Compounds represented by the above formula when R" is H or formyl, except for leurocristine and N-desformyl leurocristine which are obtained from leaves of *Vinca rosea* or which, in the case of N-desformyl leurocristine, can also be produced by deformylation of leurocristine, are prepared in one of two ways. First, the N-methyl group of vincadioline, deoxy VLB "A", leurocolumbine, psuedo VLB, etc. (in fact, any compound represented by the above formula I in which R" is methyl and R' is methoxy) can be oxidized with chromium oxide in aqueous acetic acid at −60° C. to yield a mixture of compounds in which R" is H or formyl, according to the procedure set forth in U.S. Pat. No. 3,899,493. The N-desmethyl or N-formyl compound thus formed can then be transformed into a C-3 carboxamide by the processes described herein. Alternatively, in many instances, a C-3 carboxamide can be formed with vincadioline, deoxy VLB "A", 4-desacetoxy-3'-hydroxyvinblastine, etc. as described herein and the low temperature chromic acid oxidation carried out thereon to yield a compound in which R is an amine moiety and R" is H or formyl. The above procedure is equally applicable to starting materials in which R' is methoxy or to 1-desmethyl C-3 carboxamides provided, as will be recognized by those skilled in the art, that a formylation reaction cannot be carried out with certain reactive groupings in the molecule, e.g., hydrazide, hydroxyalkyl, aminoalkyl, etc. without first protecting the reactive group.

Illustrative compounds coming within the scope of this invention include:

3'-hydroxy-4-desacetoxyvinblastine C-3 N-methyl carboxamide
3'-hydroxy-4-desacetoxyleurocristine C-3 N-cyclopropylmethyl carboxamide
2'-hydroxy-4-desacetoxyvinblastine C-3 N-cyanoethylamide
2'-hydroxy-4-desacetoxyleurocristine C-3 N-(2-hydroxypropyl)amide
4-desacetyl deoxy VLB "A" C-3 carboxazide
deoxy VLB "A" C-3 N-(2-dimethylaminoethyl) carboxamide
deoxy VLB "B" C-3 N-(2,3-dihydroxypentyl) carboxamide
C-1 formyl 4-desacetyl deoxy VLB "B" C-3 carboxhydrazide
4-desacetoxyvinblastine C-3 N-(3-hydroxypropyl) carboxamide
4-desacetoxyleurocristine C-3 N-(2-aminoethylamino) carboxamide
2'-hydroxyvinblastine C-3 N-(2-acetoxyethyl) carboxamide
2'-hydroxyleurocristine C-3 N-(2-phenylethyl) carboxamide
2'-hydroxyleurosidine C-3 N-(3-phenylpropyl) carboxamide
3'-hydroxyleurosidine-4-desacetyl C-3 carboxhydrazide
3'-hydroxy-4-desacetyl C-1 formyl leurosidine C-3 carboxhydrazide and the like.

The particular derivatives which are the subject of this invention are those in which the carbomethoxyl group at C-3 of certain known indole-dihydroindole alkaloids obtained either from plants or by partial total synthesis is transformed to a carboxhydrazide group, a carboxazide group, a carboxamide group or a derivative thereof. Not all of these derivatives are ordinarily prepared by a single process. For example, the compounds of this invention in which R is formula I above is $NH_2$, $NH-NH_2$ or $NH-CH_3$ can be prepared as follows: Treatment of VLB, leurocristine, leurosidine, leurocolumbine, vincadioline, their respective 4-desacetyl or 1-desmethyl compounds or deoxy VLB "A" or "B" or their 1-desmethyl compounds, with either ammonia, methylamine or hydrazine yields the corresponding amide, N-methylamide or hydrazide. The product of this reaction with starting materials having an intact 4-acetyl group is usually a mixture of compounds in which the carbomethoxy group at C-3 is transformed to a carboxamide, N-methylcarboxamide or carboxhydrazide group, but also in which the acetyl group at C-4 is completely or partially removed. For purification, the C-4 desacetyl derivatives thus prepared are separated by chromatography. The same amides can also be prepared by the procedure below.

The compounds of this invention in which R is $N(CH_3)_2$, NH-alk-X wherein X is H, CN, phenyl, $NH_2$, $NHCH_3$, $N(CH_3)_2$, SY', carboxyl, carboxamide or carboxyl ester, $NH-(C_3-C_8)$-cycloalk, $NH-CH_2-Y$ wherein Y is

CN or $CH(O-C_1-C_3$-alkyl$)_2$, pyrrolidinyl, NH-alk-$(OH)_{1-3}$ and alk, Y' and Z are as previously defined are conveniently prepared by the following procedure: a hydrazide, I wherein R is $NH-NH_2$ and R' is OH or H, prepared by reaction of the C-3 carbomethoxyl compound with anhydrous hydrazine, is transformed into the corresponding azide by treatment with nitrous acid, nitrosyl chloride, nitrogen tetroxide, amyl nitrite or a similar reagent according to conventional procedures. The C-3 azides thus prepared is then reacted with a suitable primary or secondary amine or ammonia: $HN(CH_3)_2$, $NH_2CH_3$, $NH_3$, $H_2NCH_2Y$, pyrrolidine, $NH_2$-alk-X, $NH_2-(C_3-C_8)$-cycloalk, $NH_2$-alk-$(OH)_{1-3}$ etc. to yield the desired C-3 amide of this invention coming within the scope of I above but usually lacking the R' acetyl group. This C-3 azide-amine reaction affects the C-4 acyl group which usually does not remain intact during the reaction and workup but can be replaced as set forth below. The above azide-amine transformation follows the procedure originated by Stoll and Huffman, Helv. Chim. Acta., 26, 944 (1943)—see also U.S. Pat. Nos. 2,090,429 and 2,090,430.

When R is $NH-C_2-C_6$ alk-$S-Y^1$ and Y' is hydrogen, the N-2-(mercapto ethyl) amide undergoes oxidation in air, particularly in the presence of base, to yield the corresponding disulfide:

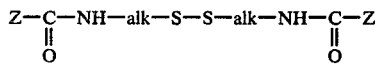

wherein Z is the residue of a dimeric indole-dihydroindole alkaloid of formula I above having a carboxamide group at C-3. Using the standard azide synthetic procedure the mercaptoethylamides and their corresponding disulfides are usually isolated as a mixture readily separable by chromatography. A synthesis of the mercaptoethylamide free from accompanying disulfide involves the reaction of a C-3 azide with $NH_2$-alk-S-trityl, where trityl is a triphenylmethyl radical. Treatment of the C-3 N-tritylmercaptoalkyl carboxamide with a heavy metal salt such as mercuric acetate followed by removal of the metal as an insoluble sulfide yields the desired mercaptoalkylamides (NH-alk-SH) substantially free from disulfide. Tris (substituted phenyl)methyl derivatives can also be used.

Compounds in which there is an acetyl group at C-4 can be prepared, as has been stated above, by reaction of VLB, leurocristine, vincadioline, leurocolumbine, deoxy VLB "A" and "B" or leurosidine directly with ammonia, methylamine or hydrazine followed by separation of the 4-acetyl derivative from the 4-desacetyl derivative, and, in the case of the hydrazide, conversion to the azide followed by reaction of the azide with an amine to yield the amides of this invention. More generally, however, because of the lability of the 4-acetyl group under basic reaction conditions, the hydrazine-azide-amide reaction sequence is carried out with a 4-desacetyl derivative. In general, the 4-desacetyl amides according to I above are reacylated with an aliphatic anhydride or acid chloride to yield the corresponding C-4 acetate, propionate or butyrate or a chloro derivative thereof. An acid chloride $(C_1-C_3)$-alkyl-COCl or chloro-$(C_1-C_3)$-alkyl-CO—Cl or an acid anhydride $[(C_1-C_3)$-alkyl-CO]$_2$=O or [chloro-$(C_1-C_3)$-alkyl-CO]$_2$=O can be used in the acylation reaction. The preferred acylation procedure is that described in U.S. Pat. No. 3,392,173 for VLB or leurocristine in which a diacyl derivative is the first product of the reaction, and this derivative is selectively hydrolysed to yield a 4-acyl compound. Other procedures involving selective acylating or multiple acylation followed by selective hydrolysis can be employed to prepare the 4-acyl derivative of this invention.

There are, however, certain provisos which must be kept in mind when an acylation procedure is contemplated. In the first place, as will be obvious to those skilled in the art, acylation of 1-desformyl leurocristine (1-desmethyl VLB), 1-desmethyleurosidine, 1-desmethylvincadioline, leurocolumbine or deoxy VLB "A" or "B" will result in acylation also at N-1. Therefore, a 1-desformyl or 1-desmethyl compound must be formylated or alkylated to give the desired substituent at N-1 prior to the C-4 acylation procedure. In addition, if the C-3 carboxamide group contains an acylable group; i.e., hydroxy or amino, the C-4 acylation procedure must be carried out prior to the azide-amine reaction which yields the ultimate C-3 carboxamide group. The preferred procedure here is to acylate at C-4, by the above procedures, the C-3 carboxhydrazide, first protecting the hydrazide group itself, which would otherwise also be acylated. The preferred hydrazide protecting group is the propylidene group formed by reaction of the $NH_2$ portion of the hydrazide moiety with acetone. This group can be readily removed by treatment with acid or, preferably, the propylidene derivative itself can be reacted directly with nitrite to form an azide group (see U.S. Pat. No. 3,470,210, Example VII).

Other procedures involving selective acylation or multiple acylation followed by selective hydrolysis or selective protection of an acylable function followed by acylation and subsequent removal of the protecting group will be apparent to those skilled in the art.

Compounds according to formula I above in which R is NH-alk-X and X is carboxyl, carboxamido or carbo-$(C_1-C_3)$-alkoxy are prepared by reacting an amino acid, amino amide or preferably an amino ester of the structure

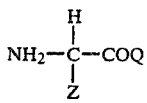

wherein Q is OH, $NH_2$ or O-alk and Z is H or a $C_1$-$C_5$ alkyl group, with the chosen dimeric indole-dihydroindole azide. Amino acids useful for this purpose, and coming within the scope of the above formula, include leucine, isoleucine, valine, glycine, alanine, norleucine and the like. As will be apparent to those skilled in the art, other amino acids and polypeptides can also be used to react with, for example, 4-desacetyl VLB C-3 carboxazide, to yield substituted C-3 carboxamides having anti-tumor properties.

Compounds in which an aldehyde amide group, $NH-CH_2-CHO$, is present are preferably prepared from the corresponding acetal amide $NH-CH_2-(O-C_1-C_3\ alkyl)_2$ by acidic hydrolysis. Compounds in which the amide group contains an ester function such as in the group $NH-(CH_2)_n-OAc$, wherein n and Ac are as defined above, are preferably prepared by esterifying an hydroxy amide containing the group $NH(CH_2)_nOH$ with a suitable acid anhydride, $Ac_2O$, wherein Ac is $C_1$-$C_{17}$-alkyl—CO or $C_2$-$C_7$-alkenyl—CO. Similarly, compounds in which R is NH—alk—X wherein X is $NH-CO-C_1-C_3$-alkyl are prepared by acylating, with an acid anhydride, an aminoalkylamide group of the structure $NH-alk-NH_2$.

While compounds represented by the above Formula I are active anti-mitotic agents and anti-tumor agents, some are also valuable as intermediates. For example, the hydrazides of Formula I can be used to prepare the corresponding azides which are in turn used to prepare other amides directly. Similarly, the hydroxyalkylamides and aminoalkylamides can be acylated (with care) to form the corresponding carboalkoxy or acylamidoalkyl amides. The acetalamides are, of course, hydrolyzed with acid to yield the corresponding acetaldehydeamides. Ohter interconversions utilizing compounds according to Formula I above as intermediates will readily suggest themselves to those skilled in the art. Certain of the compounds, for example, the azides and the 2-aminoethylamides have a low therapeutic index for anti-tumor or testing and their predominant use is as intermediates.

An alternative and presently preferred method of preparing a primary amide (R is $NH_2$) from the hydrazide (R is $NH-NH_2$) involves the use of a procedure based on that of Ainsworth, U.S. Pat. No. 2,756,235, in which the hydrazide is hydrogenolyzed with Raney nickel.

The novel derivatives of this invention will be named with reference only to the new group formed at a given carbon atom. For example, the compound produced by replacing the methyl ester function in VLB at C-3 with an amide function will be called simply VLB C-3 carboxamide, and not VLB C-3 descarbomethoxy C-3 carboxamide.

The compounds of this invention, in the form of their free bases, including both carboxamides, carboxazides and carboxhydrazides are white or tan-colored amorphous solids. It is preferable, however, where possible, to isolate and crystallize the amides in the form of their anionic salts formed with non-toxic acids. Such salts are high-melting, white, crystalline or amorphous, water-soluble solids.

The preparation of the compounds of this invention is more fully illustrated in the following specific examples:

EXAMPLE 1

VLB C-3 N-methyl carboxamide and 4-desacetyl VLB C-3 N-methylcarboxamide

A solution containing 21 g. of methylamine was prepared in 100 ml. of anhydrous methanol at $-78°$ C. About 3.5 g. of VLB were added to this solution. The reaction vessel was sealed and placed in a constant temperature bath at 50° C. for eight days. The reaction vessel was then opened, and the volatile contents removed by evaporation in vacuo. The nmr and infrared spectra of the residue indicated that it was a mixture of 4-desacetyl VLB C-3 N-methylcarboxamide and of 4-desacetyl VLB. The residue was dissolved in 100 ml. of pyridine, and 20 ml. of acetic anhydride were added. The resulting solution was allowed to stand at ambient temperature for about 18 hours. The volatile constituents were removed by evaporation in vacuo, and the resulting residue chromatographed over alumina using an ethyl acetate-chloroform (1:1) solvent mixture as the eluant. Fractions containing VLB C-3 N-methylcarboxamide as indicated by thin layer chromatography were combined, and the solvent evaporated therefrom in vacuo.

The above acetylation procedure not only reacetylates the C-4 hydroxyl but also acetylates the C-3 hydroxy. The acetyl group at C-3 was removed by the procedure of Hargrove, *Lloydia*, 27, 340 (1964), in which procedure the product containing C-3 acetylated material is treated with silica gel in aqueous methanol at room temperature for a period varying from 6 hours to several days to yield a product lacking the C-3 acetyl function. In this particular instance, the residue from the combined chromatographic fractions was dissolved in 50 ml. of methanol. Twenty ml. of water and 2 g. of silica gel were added. The resulting mixture was filtered, the filtrate evaporated to dryness in vacuo, and the resulting residue chromatographed over silica gel. A benzene-chloroform-triethylamine (100:50:7.5) solvent mixture was used as the eluant. Fractions containing the desired VLB C-3 N-methylcarboxamide were collected, and the solvent removed therefrom by evaporation in vacuo. The residue was dissolved in aqueous methanol, and the pH adjusted to 2.9 with 1 percent sulfuric acid. Evaporation of the resulting mixture in vacuo yielded VLB C-3 N-methylcarboxamide sulfate which crystallized from anhydrous ethanol to yield material melting with decomposition at 272°-5° C.

An infrared spectrum of VLB C-3 N-methylcarboxamide base obtained as indicated above showed a band at 1672 $cm^{-1}$ (absent in the spectrum of VLB) indicative of the presence of an amide group. The nmr spectrum was in complete agreement with the proposed structure of VLB C-3 N-methylcarboxamide including the newly introduced N-methylcarboxamide function which is represented by the sharp methyl resonance at 2.81 ppm.

4-Desacetyl VLB C-3 N-methylcarboxamide was isolated from the mixture with 4-desacetyl VLB obtained in the amidation step by the following procedure. The residue obtained by evaporation of the original (prior to reacetylation) reaction mixture to dryness in vacuo was chromatographed over silica gel using as eluant the benzene-chloroformtriethylamine solvent system referred to above. Fractions shown by thin layer chromatography to contain 4-desacetyl VLB C-3 N-methylcarboxamide were combined and the solvent evaporated therefrom in vacuo to yield the N-methyl carboxamide as an amorphorus solid. An infrared spectrum of the compound showed a band at 1672 cm$^{-1}$ characteristic of an amide group. The absence of the 4-acetyl group was evidenced by the lack of a resonance for this function at 2.1 ppm in the nmr (present in the nmr spectrum of VLB). The molecular weight determined by mass spectroscopy was 767 which is in agreement with the theoretical value calculated for $C_{44}H_{57}N_5O_7$.

The sulfate salt of 4-desacetyl VLB C-3 N-methylcarboxamide was prepared by the procedure described for the preparation of VLB C-3 N-methylcarboxamide sulfate. The resulting product was an amorphous, water soluble solid.

Following the above procedure, 2 g. of 4-desacetyl VLB were dissolved in a mixture of 75 ml. of anhydrous methanol and 20 g. of ethyl amine. The reaction mixture was sealed and heated at about 60° C. for about 8 days. 4-Desacetyl VLB C-3 N-ethylcarboxamide thus obtained was separated by thin layer chromatography. The resulting solid showed a band at 1670 cm$^{-1}$ in the infrared spectrum characteristic of the substituted carboxamide function.

EXAMPLE 2

Preparation of 4-desacetyl VLB C-3 carboxamide

About 10 g. of VLB sulfate were converted by standard procedures to VLB free base. The free base, obtained as a residue after evaporation of the dried ethereal solvent, was dissolved in about 200 ml. of anhydrous methanol. Anhydrous liquid ammonia (300 ml.) was added, and the reaction mixture sealed and maintained at about 100° C. for 60 hours. The reaction vessel was opened, and the contents removed and evaporated to dryness in vacuo. The resulting residue, containing 4-desacetyl VLB C-3 carboxamide, as shown by thin layer chromatography, were combined and the solvent evaporated therefrom in vacuo, yielding as a residue purified 4-desacetyl VLB C-3 carboxamide free base. The nmr and ir spectra of the solid free base confirmed the structure indicated. The free base showed a band in the infrared at 1687 cm$^{-1}$, characteristic of the amide function. The molecular weight of the free base determined by mass spectroscopy was 753 which is in agreement with theoretical value calculated for $C_{43}H_{55}N_5O_7$.

600 mg. of the above residue were converted to the sulfate salt in accordance with the procedure of Example 1. Evaporation of the reaction mixture to dryness yielded 4-desacetyl VLB C-3 carboxamide sulfate which crystallized from an ethanol-isopropyl solvent mixture and melted above 250° C. with decomposition. The salt was freely soluble in water.

4-Desacetyl VLB C-3 carboxamide was converted to VLB C-3 carboxamide by the procedures of Example 1 as follows: 2.8 g. of 4-desacetyl VLB C-3 carboxamide free bases were acetylated with a mixture of anhydrious pyridine and acetic anhydride. The reaction mixture was maintained for three days at room temperature. The volatile constituents were removed by evaporation in vacuo, and the resulting residue dissolved in methylenechloride. The methylenechloride solution was washed with water, dried, and evaporated to dryness in vacuo leaving as a residue VLB C-3 carboxamide. The amide was purified by chromatography over silica gel using an ethyl acetate-ethanol (1:1) solvent mixture as the eluant. Fractions shown to contain the VLB C-3 carboxamide by thin layer chromatography were combined, and the solvent removed therefrom by evaporation in vacuo, yielding as a residue VLB C-3 carboxamide free base. The free base had the characteristic amide band in the infrared occurring at about 1700 cm$^{-1}$. Molecular weight by mass spectroscopy was 795 which is in agreement with the theoretical value calculated for $C_{45}H_{57}N_5O_8$. VLB C-3 carboxamide sulfate was prepared by the method of Example 1 and crystallized from ethanol; m.p.=above 250° C.

EXAMPLE 3

4-Desacetyl VLB C-3 carboxhydrazide

Following the procedure of Example 1, 4-desacetyl VLB was heated in anhydrous ethanol with an excess of anhydrous hydrazine in a sealed reaction vessel at about 60° C. for about 18 hours. The reaction vessel was cooled, and opened, the contents removed, and the volatile constituents evaporated therefrom in vacuo. The resulting residue, comprising 4-desacetyl VLB C-3 carboxhydrazide, was taken up in methylenechloride, the methylenechloride solution washed with water, separated and dried, and the methylenechloride removed by evaporation in vacuo. The resulting residue was dissolved in a 1:1 chloroform:benzene solvent mixture and chromatographed over silica gel. The benzene-chloroform-triethylamine eluant of Example 1 was employed to develop the chromatogram. The initial chromatographic fractions contained unreacted 4-desacetyl VLB. Further fractions were found to contain 4-desacetyl 18'-descarbomethoxy VLB C-3 carboxhydrazide previously described by Neuss et al., *Tetrahedron Letters*, 1968, 783. The next fractions, found to contain 4-desacetyl VLB C-3 carboxhydrazide by thin layer chromatography, were combined, and the solvents evaporated therefrom in vacuo. The resulting solid melted at about 219°–220° C. with decomposition. 4-Desacetyl VLB C-3 carboxhydrazide thus prepared had a carbomethoxy absorption band in the IR at 1725–1735 cm$^{-1}$ thereby differentiating it from the 18'-descarbomethoxy compound of Neuss et al. supra, and a 1690 cm$^{-1}$ band in the IR attributable to the hydrazide function. Molecular weight by mass spectrography was 768 in agreement with the theoretical value calculated for $C_{43}H_{56}N_6O_7$. The nmr spectrum contained the prominent resonance at 3.6 ppm representing the methyl group of the C-18 carbomethoxy function.

Following the above procedure, 4-desacetyl leurocristine available from Hargrove U.S. Pat. No. 3,392,173 was reacted with anhydrous hydrazine in anhydrous methanol to yield 4-desacetyl 1-desformyl leurocristine C-3 carboxhydrazide, isolated as an amorphous powder. Infrared spectrum; absorption maxima at 1730 cm$^{-1}$ (ester), 1670 cm$^{-1}$ (hydrazide); molecular ion spectrum: m/e=754 (consistent for $C_{42}H_{54}N_6O_7$); nmr δ3.60 ($C_{18}$ methyl) δ3.74 ($C_{16}$ methyl) δ4.05 ($C_4$-hydrogen) δ6.34 (amide hydrogen).

EXAMPLE 4

4-Desacetyl leurocristine C-3 N-methylcarboxamide

A solution of 900 mg. of leurocristine and 473 ml. of anhydrous methanol was saturated with gaseous hydrogen chloride at about 0° C. The reaction flask was then fitted with a drying tube and warmed to room temperature. After being maintained at that temperature for about 24 hours, the volatile constituents were removed by evaporation in vacuo, and the resulting residue dissolved in water. The aqueous solution so formed was made basic with 14 N ammonium hydroxide and the alkali insoluble bases present extracted with methylenechloride. The methylenechloride extracts were combined, dried, and evaporated to dryness in vacuo. The resulting residue, comprising 4-desacetyl 1-desformyl leurocristine, was a light brown amorphous solid. Molecular weight by mass spectrography was 754 in agreement with that calculated for $C_{43}H_{54}N_4O_8$. In the infrared, an amide band at 1670 cm$^{-1}$, characteristic of the 1-formyl group, was lacking, but there was strong band at 1730 cm$^{-1}$ characteristic of ester absorption. Likewise the nmr spectrum showed peaks at 3.61 ppm and 3.85 ppm characteristic of the two carbomethoxy groups present and there was an additional peak at 4.11 ppm, characteristic of the proton at C-4.

A solution was prepared containing 500 mg. of 4-desacetyl 1-desformyl leurocristine prepared as above in 75 ml. of anhydrous methanol previously saturated with methylamine at $-78°$ C. (The quantity of methylamine present was about 20 g.). The reaction vessel was sealed and heated at 60° C. for about one week. The volatile constituents were then removed by evaporation in vacuo to yield 4-desacetyl 1-desformyl leurocristine C-3 N-methylcarboxamide, a light brown amorphous solid. Infrared spectrography of the above compound showed a strong amide band at 1668 cm$^{-1}$ in addition to an ester band at 1730 cm$^{-1}$.

4-Desacetyl 1-desformyl leurocristine C-3 N-methylcarboxamide thus prepared was formylated with a mixture of 24 ml. of 97 percent formic acid and 2 ml. of acetic anhydride. The reaction mixture was allowed to stand at room temperature for about 24 hours, after which time the volatile constituents were removed in vacuo. The residue thus obtained was dissolved in water, and the aqueous solution made basic with 14 N ammonium hydroxide. The nitrogenous bases insoluble in the alkaline solution were extracted into methylenechloride. The methylenechloride extracts were combined, dried, and the methylenechloride removed therefrom by evaporation in vacuo to yield 4-desacetyl leurocristine C-3 N-methylcarboxamide, a light brown amorphous solid having the following characteristics:

Molecular weight by mass spectrography was 781 in agreement with the theoretical value calculated for 4-desacetyl leurocristine C-3 N-methylcarboxamide, $C_{44}H_{55}N_5O_8$.

The nmr spectrum had peaks at 3.65 ppm, characteristic of the carbomethoxy group, and at 2.79 ppm, characteristic of the N-methylcarboxamide group.

Infrared spectrum contained a strong amide band at 1678 cm$^{-1}$, indicating the presence of more than one amide function in the molecule, and a characteristic ester band at 1728 cm$^{-1}$.

Following the procedure of Example 1, 4-desacetyl leurocristine C-3 N-methylcarboxamide free base was converted to the corresponding sulfate salt with one percent sulfuric acid. The sulfate was a white amorphous powder.

In the above procedure, other amide derivatives of 4-desacetyl 1-desformyl leurocristine C-3 N-methylcarboxamide can be formed by substituting acetic or propionic anhydride for the formylation reagent specified above to form the corresponding 4-desacetyl, 1-acetyl, or 1-propionyl leurocristine C-3 carboxamide derivative. Surprisingly, reacylation of a 4-desacetyl leurocristine to yield a 4-acyl derivative does not affect the 1-formyl group which remains intact during the synthetic procedure.

EXAMPLE 5

4-Desacetyl VLB C-3 carboxazide

A solution of 678 mg. of 4-desacetyl VLB C-3 carboxhydrazide (from Example 3) was prepared in 15 ml. of anhydrous methanol. About 50 ml. of 1N aqueous hydrochloric acid were added, and the resulting solution cooled to about 0° C. Approximately 140 mg. of sodium nitrite were then added, and the resulting reaction mixture stirred for 10 minutes while maintaining the temperature at about 0° C. The solution turned dark red-brown upon the addition of the sodium nitrite. The reaction mixture was next made basic by the addition of an excess of cold 5 percent aqueous sodium bicarbonate. The aqueous solution was extracted three times with methylene dichloride. 4-Desacetyl VLB C-3 carboxazide formed in the above reaction passed into the methylene dichloride.

While ordinarily the methylene dichloride solution of 4-desacetyl vinblastine C-3 carboxazide is used without further purification, an aliquot was treated as follows in order to characterize the azide: Evaporation of the methylene dichloride left the azide in an amorphous state. The azide residue was washed with ether, and the resulting suspension filtered. The residual tan powder had the following distinguishing physical characteristics: ultraviolet spectrum lambda$_{max}$=269 mu. (epsilon=16,700); shoulder at about 290 mu; 309 mu. (epsilon=7,100); infrared absorption maximum at 1690 cm.$^{-1}$ (carboxhydrazide) was absent, while the maximum at 1730 cm.$^{-1}$ was not affected. Furthermore, a sharply defined maximum at 2135 cm.$^{-1}$ was noted characteristic of the carboxazide function. The mass spectrogram revealed a molecular ion m/e=708 showing a loss of 71 mass units (H, CON$_3$) from the molecular weight calculated for $C_{43}H_{53}N_7O_7$=779.

EXAMPLE 6

4-Desacetyl VLB C-3 N-ethylcarboxamide

A solution of 4-desacetyl VLB C-3 carboxazide was prepared in methylene dichloride solution according to the above procedure from 900 mg. of 4-desacetyl VLB C-3 carboxhydrazide. The methylene dichloride solution was dried, and the volume reduced to about 20 ml.

The solution of the azide in methylene dichloride was then placed in a flask fitted with a drying tube and stirrer. 50 ml. of anhydrous ethylamine were added thereto, and the reaction mixture was stirred at room temperature for about two hours. Evaporation of the volatile constituents in vacuo yielded a tan amorphous powder which was chromatographed over silica gel. The chromatogram was developed with an ethyl acetate-anhydrous ethanol (3:1) solvent mixture. Fractions containing 4-desacetyl VLB C-3 N-ethylcarboxamide as determined by thin-layer chromatography were combined, and the solvent was removed from the combined fractions in vacuo. 450 mg. of a tan amorphous powder were obtained with the following distinctive physical characteristics: molecular ion spectrum, m/e=781 (corresponding to $C_{45}H_{59}N_5O_7$); infrared spectrum; absorption maxima at 1730 cm.$^{-1}$ (ester), 1670 cm.$^{-1}$ (amide), 3420 cm.$^{-1}$ (N-H amide), nmr. δ1.18 (triplet-β-methyl of ethyl amide group), δ3.28 (quartet-α-methylene of ethyl amide group), δ3.59 (singlet-methyl ester), 4-desacetyl VLB C-3 N-ethylcarboxamide sulfate was prepared by dissolving the above amorphous powder in anhydrous ethanol and adjusting the pH to about 4.0 with 2 percent sulfuric acid in anhydrous ethanol. Evaporation of the solvent in vacuo yielded a water-soluble tan powder comprising 4-desacetyl VLB C-3 N-ethylcarboxamide sulfate.

Following the above procedure, 4-desacetyl VLB C-3 N-isopropylcarboxamide was prepared. The compound had the following distinguishing characteristics: molecular ion spectrum, m/e=795 (corresponding to $C_{46}H_{61}N_5O_7$); infrared spectrum: maxima at 1730 cm.$^{-1}$ (ester), 1660 cm.$^{-1}$ (amide); nmr; δ1.16, δ1.22 (doublet-for isopropyl methyl groups); 4-desacetyl VLB C-3 N-isopropylcarboxamide sulfate was prepared by the above procedure and was a tan water-soluble amorphous powder.

Following the above procedure, 4-desacetyl VLB C-3 N,N-dimethylcarboxamide was prepared having the following distinctive physical characteristics: molecular ion spectrum; m/e=781 (consistent with $C_{45}H_{59}N_5O_7$; infrared spectrum: absorption maxima at 1730 cm.$^{-1}$ (ester), 1620 cm.$^{-1}$ (amide); nmr δ2.96 (singlet-N-methyl) δ3.46 (singlet-N-methyl). The sulfate salt of 4-desacetyl VLB C-3 N,N-dimethylcarboxamide was prepared by the above procedure and was a water-soluble, tan amorphous powder.

Following the above procedure, 4-desacetyl VLB C-3 N-hexylcarboxamide was prepared, a tan amorphous powder with the following physical characteristics: infrared spectrum; peaks at 3420 cm.$^{-1}$ (NH), 1665 cm.$^{-1}$ (CON), 1730 cm.$^{-1}$ (COO); nmr spectrum, peaks generally consistent with postulated formula plus additional band at δ1.15–1.45 for pentamethylenehydrogens and terminal methyl hydrogens, molecular spectrum, m/e=778, 496, 335, 154; molecular ion, M+ =837 consistent with empirical formula $C_{49}H_{67}N_5O_7$.

Following the above procedure, 4-desacetyl VLB C-3 N-cyclohexylamide was prepared as a tan amorphous powder with the following physical characteristics: infrared spectrum; peaks at 3410 cm.$^{-1}$, 1660 cm.$^{-1}$, 1730 cm.$^{-1}$; molecular spectrum, m/e=776,484,355,154; molecular ion M+ =835 consistent with empirical formula $C_{49}H_{65}N_5O_7$.

Following the above procedure, 4-desacetyl VLB C-3 N-pyrrolidinyl amide was prepared, a tan amorphous powder with the following physical characteristics: infrared spectrum; peaks at 1730 cm.$^{-1}$ (COO) and 1610 cm.$^{-1}$ (CON); molecular spectrum; m/e at 749, 466, 355, 154; molecular ion, M+ =807 consistent with empirical formula $C_{47}H_{61}N_5O_7$. The sulfate salt was also prepared, a tan amorphous powder.

Following the above procedure, 4-desacetyl VLB C-3 N-β-butyryloxyethyl amide was prepared with the following physical characteristics: infrared spectrum; peaks at 3420 cm.$^{-1}$, 1735 cm.$^{-1}$, and 1680 cm.$^{-1}$; molecular spectrum; molecular ion, M+ =867 consistent with empirical formula $C_{49}H_{65}N_5O_9$.

Following the above procedure, 4-desacetyl VLB C-3 N-(2,3-dihydroxypropyl) carboxamide was prepared as a tan amorphous powder having the following physical characteristics: infrared spectrum, peaks at 3420 cm.$^{-1}$ (NH), 1660 cm.$^{-1}$ (CON), 1730 cm.$^{-1}$ (COO). Molecular spectrum, m/e 769, 486, 455, 154, molecular ion M+ =827 consistent with empirical formula $C_{46}H_{61}N_5O_9$. The corresponding sulfate salt was prepared as set forth above and was also a tan amorphous powder.

Following the above procedure, 4-desacetyl VLB C-3 N-(2-hydroxyethyl) carboxamide was prepared by reacting 4-desacetyl VLB C-3 carboxazide with ethanol amine. It was a tan amorphous solid with the following physical characteristics: infrared spectrum; peaks at 3420 cm.$^{-1}$ (NH), 1732 cm.$^{-1}$ (COO), 1670 cm.$^{-1}$ (CON). Molecular ion M+ =797 consistent with empirical formula $C_{45}H_{59}N_5O_8$. The corresponding sulfate salt was prepared by the above procedure and was a water soluble tan amorphous powder.

4-Desacetyl VLB C-3 N-(2-acetoxyethyl) carboxamide was prepared from the N-hydroxyethyl amide by acetylation. It was a tan amorphous powder with the following physical characteristics: infrared spectrum, peaks at 3420 cm.$^{-1}$ (NH), 1740 cm.$^{-1}$ (COO), and 1670 cm.$^{-1}$ (CON). Molecular spectrum, molecular ion M+ =839 consistent with empirical formula $C_{47}H_{61}N_5O_9$; nmr spectrum consistent with structure, particularly with added peak at δ191 (acetylmethyl).

Following the above procedure, 4-desacetyl VLB C-3 N-(3-hydroxypropyl) amide was prepared, a tan amorphous powder with the following physical characteristics: infrared spectrum, peaks at 3410 cm.$^{-1}$, 1660 cm.$^{-1}$; 1730 cm.$^{-1}$; molecular spectrum, m/e=753, 470, 355, 154-molecular ion, M+ =811 consistent with the empirical formula $C_{46}H_{61}N_5O_8$. The corresponding sulfate salt was also prepared and was a tan amorphous powder.

4-Desacetyl VLB C-3 N-(2-aminoethyl) carboxamide was prepared by the above procedure and was a tan amorphous powder with the following physical characteristics: $pk_a$=6.8, 9.0, 4.6. Infrared spectrum; peaks at 3420 cm.$^{-1}$ (NH), 1730 cm.$^{-1}$ (COO), 1670 cm.$^{-1}$ (CON; molecular spectrum, molecular ion, M+ =796 consistent with empirical formula $C_{45}H_{60}N_6O_7$. A sulfate salt was also prepared as a tan amorphous powder.

Following the above procedure, 4-desacetyl VLB C-3 N-[2-(N,N-dimethylaminoethyl)]carboxamide was prepared from the carboxazide and N,N-dimethyl ethylamine. It had the following distinguishing physical characteristics: Infrared spectrum; absorption maxima at 3410 cm.$^{-1}$ (N—H amide), 1740 cm.$^{-1}$ (ester), 1670 cm.$^{-1}$ (amide); nmr δ2.44, δ3.41 (methylenes from ethylidene function) 2.33 (methyls of dimethylamino group); molecular ion spectrum; m/e=824 (consistent with $C_{47}H_{64}N_6O_7$); pKa=4.85, 7.0, 8.5. The corresponding sulfate salt prepared by the above procedure was a tan, water-soluble amorphous powder.

4-desacetyl VLB C-3 N-benzylcarboxamide was prepared using benzylamine by the above procedure and had the following distinctive physical characteristics: Infrared spectrum; maxima at 3420 cm.$^{-1}$ (N—H amide), 1735 cm.$^{-1}$ (ester), 1675 cm.$^{-1}$ (amide); nmr; 67 7.32 (aromatic protons) δ3.69 (methylene group of benzyl amide); molecular ion spectrum, m/e=843 (consistent with $C_{50}H_{61}N_5O_7$). The corresponding sulfate salt was made by the above procedure and was a water-soluble, tan amorphous powder.

Following the above procedure, 4-desacetyl VLB C-3 N-cyanomethylcarboxamide was prepared by reacting 4-desacetyl VLB C-3 carboxazide with cyanomethylamine. The novel amide had the following distinctive physical characteristics: Infrared absorption maxima at 1690 cm.$^{-1}$ (amide); 3420 cm.$^{-1}$ (amide NH); nmr; δ4.17 ($C_4$-H) δ2.80 (N-$CH_3$) δ3.77 (aromatic H) δ3.69 (methylester H) δ4.48 (J=6Hz) δ3.92 (J=17Hz);

both cyanomethylene. Molecular ion spectrum m/e=792 (consistent with $C_{45}H_{56}N_6O_7$).

Following the above procedure, 1-desformyl 4-desacetyl leurocristine C-3 carboxyhydrazide, furnished by the procedure of Example 3, was reacted with sodium nitrite in dilute hydrochloric acid to form 1-desformyl 4-desacetyl leurocristine C-3 carboxazide which was obtained as a yellow amorphous powder. A methylene dichloride solution of 1-desformyl 4-desacetyl leurocristine C-3 -carboxazide was then reacted with ethylamine to yield 1-desformyl 4-desacetyl leurocristine C-3 N-ethylcarboxamide. The compound was purified by chromatography over silica gel using an ethyl acetate-anhydrous ethanol (1:1) solvent mixture as the eluant. Fractions, determined by thin-layer chromatography to contain the N-ethyl amide, were combined, and the combined fractions evaporated to dryness. 1-desformyl 4-desacetyl leurocristine C-3 N-ethylcarboxamide was obtained as a yellow amorphous powder having the following distinctive physical characteristics: Infrared spectrum; absorption maxima at 1665 cm.$^{-1}$ (amide), 1745 cm.$^{-1}$ and 1730 cm.$^{-1}$ (ester bands, 1 hydrogen bonded), 3430 cm.$^{-1}$ (N-H amide); molecular ion spectrum; m/e=767 (consistent with $C_{44}H_{57}N_5O_7$).

Following the above procedure, 4-desacetyl VLB C-3 N-2-dimethoxyethylamide was prepared by reacting 4-desacetyl VLB C-3 carboxazide with 2-dimethoxyethylamine. The amide thus produced had the following physical characteristics: infrared absorption maxima at 1665 cm$^{-1}$ (amide) and at 1730$^{-1}$ (carboxyl); molecular ion spectrums (m/e), molecular ion at 841 other peaks at 782, 651, 500, 355, and 154; NMR δ4.42 (triplet) δ3.41 (doublet $C_1$-2H), δ3.36-3.45 (6 methyl ether hydrogens).

The sulfate salt was prepared by dissolving the free base prepared as above in methanol and adding a solution of 2 percent sulfuric acid also in methanol thereto. Evaporation of the resulting solution to dryness yielded a tan amorphous water soluble powder.

Following the above procedure, 4-desacetyl VLB C-3 N-3-cyanopropylcarboxamide was prepared by reacting 4-desacetyl VLB C-3 carboxazide with 3-cyanopropylamine (prepared from the fumarate salt by solution in water, alkalinizing, extraction into an organic solvent, drying and removal of the solvent to yield an oil). The novel amide had the following physical characteristics: molecular spectrum (m/e) molecular ion at 806, peaks at 465, 154; infrared spectrum peaks at 3400$^{-1}$ (N-H), 2265 cm$^{-1}$ (weak-cyano), 1725 cm$^{-1}$ (carboxyl) and 1680 cm$^{-1}$ (carboxamide). The nuclear magnetic resonance spectrum was consistent with the proposed structure. The sulfate salt was prepared in the usual manner.

Following the above procedure, 4-desacetyl VLB C-3 N-propargyl carboxamide was prepared by reacting 4-desacetyl VLB C-3 carboxazide with propargylamine. The compound was purified by chromatography over silica using a 1:1:1 methylene dichloride/ethyl acetate/methanol solvent mixture as eluant. The yield was 630 mg. The amide was converted to the corresponding sulfate salt in ethanol. The compound had the following physical characteristics: Titration (66 percent aqueous DMF);$pK_a$=5.33, 7.26; Infrared spectrum (in chloroform); peaks at 1730, 1675, and 3310 cm$^{-1}$; Molecular Spectrum: (m+) 791, (m/e) 450, 732, 760.

Following the above procedure, 4-desacetyl VLB C-3 N-(4-hydroxyphenylethyl)carboxamide was prepared by reacting tyramine (obtained from 10 g. of tyramine hydrochloride) with 4-desacetyl VLB C-3 carboxazide. The sulfate salt was prepared in ethanol. The compound had the following physical characteristics: Infrared spectrum (in chloroform); peaks at 3680, 3600, 3480, 3420, 1740, 1675, 1638 cm$^{-1}$; Molecular Spectrum; molecular ion at 873 (also transmethylation at m/e=887).

Following the above procedure, 4-desacetyl VLB C-3 N-(3,4-dihydroxyphenylethyl) carboxamide was prepared by reacting dopamine (obtained from 10 g. of dopamine hydrochloride) and 4-desacetyl VLB C-3 carboxazide. The compound was purified by chromatography over silica using a 1:1:1 methylene dichloride/ethyl acetate/methanol solvent system. The sulfate sale was prepared. The compound had the following physical characteristics: Molecular Spectrum; molecular ion at 899, transmethylation peaks (m/e) at 903 and 917; Infrared spectrum (in chloroform); peaks at 1740, 1680 cm$^{-1}$.

EXAMPLE 7

4-Desacetyl leurosidine C-3 carboxamide

Following the method of Example 3, 1500 mg. of leurosidine were reacted with 25 ml. of anhydrous hydrazine in anhydrous methanol solution. The reaction mixture was sealed in a reaction flask, and the flask heated to 50° C. for 12 days. Evaporation of the volatile consistuents in vacuo yielded 4-desacetyl leurosidine C-3 carboxhydrazide having the following distinctive physical characteristics: Infrared maximum 1735 cm.$^{-1}$ (ester), 1660 cm.$^{-1}$ (hydrazide); molecular ion spectrum; m/e=768 (consistent with $C_{43}H_{56}N_6O_7$).

4-Desacetyl leurosidine C-3 carboxhydrazide was converted to the corresponding azide by treatment with sodium nitrite, and the azide reacted with methanol saturated with ammonia at −78° C. to yield 4-desacetyl leurosidine C-3 amide which was purified by chromatography. The compound had the following physical characteristics: Infrared maxima at 3400 cm.$^{-1}$ (N—H amide), 1740 cm.$^{-1}$ (ester), 1690 cm.$^{-1}$ (amide); molecular ion spectrum, m/e=753 (consistent with $C_{43}H_{55}N_5O_7$); nmr; δ3.58 ($C_{18}$ methyl ester), δ3.78 ($C_{16}$, methoxy), δ2.88 ($C_1$ methyl) δ5.78 (C-3 amide hydrogens), δ4.18 ($C_4$ hydrogen). The corresponding sulfate salt was prepared by a procedure involving neutralization of an ethanol solution of the base with ethanolic sulfuric acid to yield a tan amorphous powder.

Other amides of leurosidine can be prepared in similar fashion.

Following the above procedure, 2.55 grams of deoxy VLB "B" were reacted with 30 ml. of anhydrous hydrazine in anhydrous methanol. 4-Desacetyl deoxy VLB "B" C-3 carboxhydrazide thus prepared was isolated and purified by the above procedure to yield an amorphous powder with the following characteristics: infrared maxima; 3440 cm.$^{-1}$ (N—H), 1735 cm.$^{-1}$ (COO), 1675 cm.$^{-1}$ (CON); molecular ion spectrum; m/e=752 (consistent with $C_{43}H_{56}N_6O_6$); nmr spectrum; δ3.78 (ArOC$H_3$), δ3.58 ($C_{18}$COOC$H_3$), δ2.77 (N-C$H_3$), δ4.15 ($C_4$-H).

EXAMPLE 8

4-Desacetoxyvinblastine C-3 N-2-Hydroxyethylcarboxamide

Following the procedure of Example 3, 4-desacetoxyvinblastine was reacted with anhydrous hydrazine in methanol solution is a sealed tube at 46° C. for three days. 4-Desacetoxyvinblastine C-3 carboxyhydrazide thus prepared was isolated and purified by the procedure of the same example. The compound had the following physical characteristics: $pK_a=5.61$ and 7.38; ultraviolet spectrum; $\lambda max=215$ and 267 nm; infrared spectrum, peaks at 3450 cm.$^{-1}$ (N—H), 1725 cm.$^{-1}$ (COO), 1680 cm.$^{-1}$ (CON); molecular spectrum m/e=252, 411, 355, 244, 154. Molecular ion M+=752 consistent with empirical formula $C_{43}H_{56}N_6O_6$. The compound was a tan amorphous powder.

Following the procedure of Example 5, 4-desacetoxyvinblastine C-3 carboxyhydrazide was converted to the corresponding carboxazide in hydrochloric acid solution at 0° C. with sodium nitrite. The azide was isolated and purified by the procedure of that example.

Following the procedure of Example 6, 5 ml. of ethanol amine were added to a solution containing about 1.2 g. of 4-desacetoxyvinblastine C-3 carboxazide. The reaction mixture was sealed and protected from light. After being allowed to stand for one day at room temperature, the reaction vessel was opened and the volatile constituents removed from the reaction mixture by evaporation in vacuo. The resulting residue containing 4-desacetoxyvinblastine C-3 N-(2-hydroxyethyl) carboxamide formed in the above reaction was dissolved in methylene dichloride and the methylene dichloride layer washed several times with water. The methylene dichloride layer was separated and dried and the solvent removed by evaporation in vacuo. The resulting residue was chromatographed over silica gel using a 3:1 ethyl acetate-ethanol solvent mixture as the eluant. Fractions shown to contain the desired product as determined by thin layer chromatography were combined and evaporated to dryness in vacuo. 4-Desacetoxyvinblastine C-3 N-(2-hydroxyethyl) carboxamide thus prepared was a tan amorphous material with the following physical characteristics: molecular ion; M+=781 consistent with empirical formula $C_{45}H_{59}N_5O_7$; infrared spectrum peaks at 3420 cm.$^{-1}$ (NH), 1735 cm.$^{-1}$ (COO), 1665 cm.$^{-1}$ (CON). The sulfate salt was prepared using ethanolic sulfuric acid and adjusting the pH in the range 3.8-4.2. The sulfate salt was recovered by evaporation of the volatile constituents in vacuo.

Following the above procedure, 4-desacetoxyvinblastine C-3 amide was prepared by reacting the carboxazide with ammonia in ethanol solution. 4-Desacetoxyvinblastine C-3 amide was a tan amorphous powder with the following physical characteristics: molecular ion; M+=737 consistent with empirical formula $C_{43}H_{55}N_5O_6$; other molecular spectrum peaks at 737, 396, 295, 154; infrared spectrum peaks at 3510 and 3400 cm.$^{-1}$ (amide-NH$_2$), 1725 cm.$^{-1}$ (COO), 1690 cm.$^{-1}$ (CON).

Following the above procedure, 4-desacetoxyvinblastine C-3 N-isopropyl carboxamide was prepared from the 4-desacetoxyvinblastine C-3 carboxazide with isopropylamine. The compound was a tan amorphous powder with the following physical characteristics: molecular spectrum, m/e=779 consistent with empirical formula $C_{46}H_{61}N_5O_6$; infrared spectrum peaks at 3410 cm.$^{-1}$ (NH), 1730 cm.$^{-1}$ (COO), 1675 cm$^{-1}$ (CON); nmr doublets at $\delta 1.18$ (isopropyl methyls), $\delta 6.89$ (amide-hydrogen).

Each of the desacetyl 1-desformyl 1-alkanoyl derivatives, as well as the 4-desacetyl VLB, leurocristine, or leurosidine C-3 carboxamides with exception of the carboxyhydrazides and those amide moieties containing a reactive function as discussed above, can be reacted with other anhydrides such as chloroacetic acid anhydride, butyric anhydride, 2-chloropropionic anhydride and the like to yield using, for example, chloroacetic anhydride, a mixture of the 3,4-bischloroacetyl and the 4-chloroacetyl derivatives which can be converted to the pure 4-chloroacetyl derivative by treatment with wet silica gel. Other 4-acyl derivative of this invention are prepared in similar fashion.

EXAMPLE 9

4-Desacetylvincadioline C-3 N-Methylamide

Following the procedure of Example 7, vincadioline was reacted with hydrazine to form the corresponding C-3 carboxyhydrazide. The hydrazide was in turn converted to the corresponding carboxazide by the procedure of Example 8 and the azide was reacted with methylamine according to the procedure of the same example. The product of this reaction, 4-desacetyl vincadioline C-3 N-methylamide, had the following physical characteristics: infrared spectrum peaks at 2.95 m$\mu$, 5.75 m$\mu$ and 5.97 m$\mu$; nmr spectrum consistent with postulated structure with added doublet at $\delta 3.82$ (amide-methyl hydrogens); molecular spectrum, molecular ion M+=783 consistent with $C_{44}H_{57}N_5O_8$. The N-methylamide. of 4-desacetyl leurocolumbine (3'-hydroxy VLB) is prepared in similar fashion from leurocolumbine via the hydrazide and aside.

EXAMPLE 10

4-Desacetyl VLB C-3 N-Acetaldehydecarboxamide

4-Desacetyl VLB C-3 N-2-dimethoxyethylcarboxaide prepared by the procedure of Example 6 was dissolved in 1 N aqueous hydrochloric acid. The reaction mixture was allowed to stand at room temperature for 4 hours and was then made basic with 14 N aqueous ammonium hydroxide. The amide, being insoluble in the alkaline solution, separated and was extracted into methylene dichloride. The methylene dichloride layer was separated, dried, and the solvent removed by evaporation. Chromatography of the residual powder over silica gel using a 3:1 ethyl acetate-ethanol solvent mixture as the eluant yielded purified 4-desacetyl VLB C-3 N-acetaldehydecarboxamide having the following physical characteristics: $R_f=0.43$ (compared with $R_f=1.50$ for dimethylacetal). Infrared spectrum:peaks at 3420 cm$^{-1}$ (N—H), 1735 cm$^{-1}$ (carboxyl), 1675 cm$^{-1}$ (carboxamide); nmr $\delta 7.78$ (tripletamide H) $\delta 9.67$ (aldehyde H).

The sulfate salt was prepared by dissolving the above amide in absolute ethanol and adjusting the pH of the resulting solution to 5.0 with 2 percent sulfuric acid in absolute ethanol. Evaporation of the solvent to dryness yielded the sulfate salt as a tan amorphous powder.

EXAMPLE 11

4-Desacetyl VLB C-3 N-2-acetylaminoethylcarboxamide

A solution was prepared with 1600 mg. of 4-desacetyl VLB C-3 N-2-aminoethylcarboxamide as provided by Example 6 in 30 ml. of methylenedichloride to which was added 5 ml. of pyridine. 200 mg. of acetic anhydride were next added. The reaction vessel was sealed and the reaction mixture stirred at ambient temperature for 24 hours. Methanol was then added to react with excess anhydride. The volatile constituents were removed by evaporation, and the residue, comprising 4-desacetyl VLB C-3 N-2-acetylaminoethylcarboxamide, was dissolved in methylene dichloride. The methylene dichloride layer was washed several times with dilute aqueous ammonium hydroxide followed by a water wash. The methylene dichloride layer was dried, and the methylene dichloride evaporated therefrom. Chromatography of the resulting residue on silica gel using a 1:1 ethyl acetatemethanol solvent mixture yielded purified 4-desacetyl VLB C-3 N-2-acetylaminoethylcarboxamide having the following physical characteristics: Molecular spectrum (m/e) molecular ion=838 consistent for $C_{47}H_{62}N_6O_8$. Infrared spectrum; peaks at 3429 cm$^{-1}$ (N—H), 1735 cm$^{-1}$ (carboxyl), 1670 cm$^{-1}$ (amide). nmr showed peaks at $\delta$4.17 and 1.965 (acetyl hydrogens on $\beta$-amino group).

EXAMPLE 12

4-Desacetyl VLB C-3 N-2-Acrylyloxyethylcarboxamide

A solution was prepared containing 1100 mg. of 4-desacetyl VLB C-3 N-2-hydroxyethylcarboxamide from Example 8 in 50 ml. of benzene. 150 mg. of acrylyl chloride were added. The reaction vessel was sealed and the reaction kept at ambient temperature for 18 hours. The reaction vessel was then opened and 200 mg. of acrylyl chloride were added. The reaction vessel was again sealed and maintained at ambient temperature for 10 additional hours. The reaction vessel was then opened and the reaction mixture worked up by contacting the organic solution with dilute ammonium hydroxide to remove any excess acid chloride. The organic layer was then dried and the solvents evaporated therefrom. Chromatography of the residue comprising 4-desacetyl VLB N-2-acrylyloxyethylcarboxamide with 3:1 ethyl acetate-ethanol solvent mixture over silica gel yielded purified amide (27 mg.) as a tan amorphous powder with the following physical characteristics: Molecular spectrum (m/e) molecular ion=851 consistent with $C_{48}H_{51}N_5O_9$. Infrared spectrum peaks as follows: 3427 cm$^{-1}$, (NH), 1730 cm$^{-1}$ (carboxyl), 1675 cm$^{-1}$ (amide).

Following the above procedure but substituting stearic anhydride for acrylyl chloride, 4-desacetyl VLB C-3 N-2-stearoyloxyethylcarboxamide was prepared having a molecular ion at 1063 consistent with $C_{63}H_{93}N_5O_9$ and others peaks at 1004, 651, 355 and 154. The sulfate was prepared in the usual manner using anhydrous ethanol. The resulting sulfate salt was a tan amorphous powder insoluble in water.

EXAMPLE 13

Alternate Preparation of 4-Desacetyl VLB C-3 Carboxamide

A slurry was prepared with 1 kg. of fresh Raney nickel and 6 l. of methanol in a 12 l. Morton flask fitted with thermometer, stirrer, and condenser. A solution of 200 g. of 4-desacetyl VLB C-3 carboxhydrazide dissolved in 3 l. of methanol was added thereto. The reaction mixture was heated to reflux for about 7 hours. The reaction mixture was then filtered by decantation through about ½ inch of talc spread on a 24 cm. Buchner funnel. The Raney nickel remaining behind in the flask was washed 4–5 times with 1 liter portions of anhydrous methanol. The filtrate was evaporated to a volume of about less than 1 l. During this concentration process, 4-desacetyl VLB C-3 carboxamide thus formed began to crystallize. The solution was transferred to a flask, and the flask with contents refrigerated overnight. Filtration of the crystalline material yielded 179.4 g. (wet weight) of 4-desacetyl VLB C-3 carboxamide. The filtrate was concentrated and yielded an additional 53.3 g. of compound (wet weight). Total yield equals 86.9 percent.

EXAMPLE 14

Preparation of 4-desacetyl VLB C-3 N-(2-mercaptoethyl)carboxamide and bis-[$\beta$-(4-desacetyl VLB C-3 carboxamido)ethyl]disulfide.

12 Gms. of 4-desacetyl VLB C-8 carboxhydrazide were converted to the azide by the procedure of Example 5. Next, 68.2 g. of 2-mercaptoethylamine hydrochloride were dissolved in a minimum amount of water and the resulting acidic solution made alkaline with concentrated aqueous sodium hydroxide. 2-Mercaptoethylamine free base thus formed, being insoluble in the alkaline layer, separated and was extracted with ethyl acetate. The aqueous layer was further extracted with ether and with methylene dichloride. The organic extracts were combined, and the solvents removed therefrom by evaporation. The residual amine was dissolved in a minimal quantity of methylene dichloride and this solution added to a solution of the azide, prepared as above, in 500 ml. of methylene dichloride. The reaction mixture was heated on the steam bath for five minutes and then cooled. 20 ml. of pyridine were added and the mixture stirred overnight at room temperature. Next, an excess of five percent aqueous sodium bicarbonate were added and the organic and aqueous layers separated. The organic layer was washed three times with water and then dried. The solvent was removed by evaporation in vacuo. The residue, comprising a mixture of 4-desacetyl VLB C-3 N-(2-mercaptoethyl) amide and bis[$\beta$-(4-desacetyl VLB C-3 carboxamido)ethyl] disulfide formed in the above reaction and work-up were separated by high pressure liquid chromatography over silica using a 1:1:1 methylene dichloride/ethyl acetate/methanol solvent mixture containing 2 percent triethylamine. Two fractions were obtained, one with $R_f$=0.5 and a second with $R_f$=0.25. Both fractions had several virtually identical physical chemical properties as follows: Molecular Spectrum: m/e=827 (molecular ion+-transmethylation), 486; Infrared Spectrum: peaks at 1730 and 1670 cm$^{-1}$ (in chloroform); NMR-virtually superimposable.

The fractions were differentiated as to structure by the following criteria: The faster moving material referred to as $R_f$=0.5 fraction had three titratable groups, pKa (in 66 percent aqueous dimethylformamide) at 5.3, 7.38, and 11.8. The slower moving fraction, $R_f$=0.25, had only two titratable groups, these occurring at pKa=5.2 and 7.5. The $R_f$=0.5 fraction thus had an extra titratable group which would be the sulfhydryl group of the C-3 amide. This SH group is, of course, missing in the disulfide which was the $R_f$=0.25 fraction. In addition, $^{13}$C NMR analysis indicated that both fractions had peaks in the 173.6–173.8 region consistent with a secondary amide carbon (vindesine—a C-3 carboxamide and also a primary amide—has a peak at 176.7). Both samples had many identical peaks and only two extraneous peaks the $R_f$=0.5 fraction at 42.3 and 24.2 and the $R_f$=0.25 nonidentical at 38.0 and 37.6. An interpretation of the $^{13}$C NMR spectrum fraction indicates that the former peaks are consistent with the two carbons in the ethyl side chain when unsubstituted (mercaptoethyl amide) and the latter peaks are consistent with the same ethyl side chain interpretation except that the sulfur is substituted (as in a disulfide). Molecular weight by osmotic determination for the $R_f=0.25$ fraction was 1770 (calculated=1624) again consistent with a disulfide structure. Sulfhydryl analysis for the $R_f=0.5$ fraction was 0.8 and for the $R_f=0.25$ fraction 0.

EXAMPLE 15

Alternate Preparation of 4-desacetyl VLB C-3 N-(2-mercaptoethyl)carboxamide

A mixture of 11.3 g. of 2-mercaptoethylamine hydrochloride and 39 g. of tris (4-methoxyphenyl)methyl chloride were stirred overnight in 300 ml. of DMF. The solution was poured over 1 l. of an ice-water mixture and the aqueous solution was extracted with ether to remove tris (4-methoxyphenyl)methyl alcohol present. The aqueous layer was then made basic (pH=8.4) with 5 percent aqueous sodium bicarbonate. The alkaline mixture was extracted four times with methylene dichloride. The methylene dichloride extracts were combined and the combined extracts washed with water and dried. Removal of the solvent in vacuo left a residual oil which was again washed with water to remove any remaining DMF. The resulting residue was dissolved in methylene dichloride and chromatographed over silica using a 1:1 methylene dichloride/ethyl acetate solvent mixture as the eluant. After a forerun containing eluted tris (4-methoxyphenyl)methyl alcohol, fractions containing tris-[(4-methoxyphenyl)methylthio]ethylamine formed in the above reation were collected, combined, and the solvent removed therefrom in vacuo. 7.0 g. of the compound were obtained as a gum.

Analysis Calc: C, 70.39; H, 6.65; N, 3.42; S, 7.83. Found: C, 70.35; H, 6.45; N, 3.29; S, 7.75.

Titration: (66 percent aqueous DMF) $pK_a=8.91$ giving a molecular weight=466.

Ultraviolet spectrum (in methanol): maxima at 234 and 276 ($\epsilon=26,000$ and 5,000 respectively).

NMR in deuterochloroform: $\delta$ at 1.24, 2.49, 3.80, 7.07.

5 Gms. of 4-desacetyl VLB C-3 carboxhydrazide were converted to the azide by the procedure of Example 5. 4 G. of tris-[(4-methoxyphenyl)methylthio]ethylamine were added to a solution of 4-desacetyl VLB C-3 carboxazide in methylene dichloride and the resulting mixture was stirred overnight at ambient temperature. The reaction mixture was washed once with water and then dried. The solvent was removed by evaporation in vacuo. The resulting residue, containing 4-desacetyl VLB C-3 N-($\beta$-[tris-(4-methoxyphenyl)methylthio]ethyl)carboxamide formed in the above reaction was purified by chromatography over silica using a 1:1:1 methylene dichloride-ethylacetate-methanol solvent mixture as eluant. Fractions containing the amide were combined and the solvent removed therefrom in vacuo. The resulting residue was triturated with ether to remove traces of tris-(4-methoxyphenyl)methyl methyl ether. The amide had the following physical characteristics:

Infrared spectrum (in chloroform): peaks at 1715, 1660, 1600 cm$^{-1}$.

Molecular spectrum: peak at 827 (free mercapto plus transmethylation) and 333 (tris-(4-methoxyphenyl)-methyl radical.

NMR in deuterochloroform: $\delta$ at 6.75, 6.84, 7.24, 7.33 (almost identical in pattern and chemical shift to the starting amine).

113 mg. of 4-desacetyl VLB C-3 N-(2-[tris-(4-methoxyphenyl)methylthio]ethyl) carboxamide were added to a solution of 32 mg. of mercuric acetate in 2 ml. of anhydrous ethanol. The reaction mixture was stirred at ambient temperature for 30 minutes and the solvent then removed by evaporation. The resulting residue was washed with ether and the ether layer separated. The residue was then dissolved in anhydrous ethanol, and the ethanol solution cooled to about 0° C. Hydrogen sulfide gas was bubbled into the ethanolic solution for about 30 minutes. The solution was then filtered to remove mercuric sulfide and the filtrate evaporated in vacuo. The resulting residue was dissolved in methylene dichloride. The solution was again filtered and the methylenedichloride removed in vacuo. Thin layer chromatography over silica using a 1:1:1 methylene dichloride-ethyl acetate-methanol solvent system showed a single alkaloidal spot at $R_f=0.5$ with a higher non-alkaloidal spot at $R_f=0.83$ (probably tris-(4-methoxyphenyl)methyl ethyl ether). The starting material had $R_f=0.72$. 4-desacetyl VLB C-3 N-(2-mercaptoethyl)carboxamide thus prepared was purified from non-alkaloidal material by chromatography over silica using the above solvent system as eluant.

4-Desacetyl VLB-C-3 N-(2-mercaptoethyl)carboxamide prepared as above was identical to the $R_f=0.5$ material obtained in Example 14, in further substantiation of the structure assignments made therein. It is believed that the primary product of the reaction between the 4-desacetyl VLB C-3 carboxazide and 2-mercaptoethylamine is the corresponding 2-mercaptoethylamide ($R_f=0.5$ fraction) but that this compound is oxidized to the disulfide ($R_f=0.25$ fraction) by atmospheric oxygen under basic reaction conditions which would include both the utilization of pyridine in the reaction itself and the use of such mild bases as sodium bicarbonate in the workup and purification of the products of the initial reaction.

The above series of reactions can be repeated employing trityl chloride in place of tris-(4-methoxyphenyl) methyl chloride. 2-Trityl thioethylamine was reacted with 4-desacetyl VLB C-3 carboxazide to yield 4-desacetyl VLB C-3 N-(2-tritylthioethyl) carboxamide. The corresponding sulfate salt was also prepared in ethanol. The tritylated derivative was then coverted to the corresponding free mercaptoethylamide by reaction with mercuric acetate as above.

EXAMPLE 16

Preparation of salts

Other salts, including salts with inorganic anions such as chloride, bromide, phosphate, nitrate and the like as well as salts with organic anions such as acetate, chloroacetate, trichloroacetate, benzoate, alkyl or aryl sulfonates and the like, are prepared from the amides bases of this invention by a procedure analogous to that set forth in Example 1 above for the preparation of the sulfate salt by substituting the appropriate acid in a suitable diluent in place of the 2 percent aqueous sulfuric acid of that example.

As will be apparent to those skilled in the art. The presence of other ester and/or amide groups in the indole-dihydroindole compounds of this invention requires extra care in the preparation of salts so as to avoid hydrolysis, transesterification and other reactions which take place at high temperatures, at extremely acid pH's etc.

The compounds of this invention have shown antiviral activity in vivo against the Freund leukemia virus and in vitro against herpes virus. In this latter test, a tissue culture system in a plaque suppression test similar to that described by Siminoff, *Applied Microbiology*, 9, 66–72 (1961) was employed. For example, VLB C-3 carboxamide sulfate gave a 20 mm inhibition zone with a 3 rating and without toxicity at a dose level of 125 μg/ml. The same compound was shown to be able to induce metaphase arrest in cultured Chinese hampster ovary cells at doses ranging from $2 \times 10^{-2}$ μg/ml. to $2 \times 10^{-5}$ μg/ml. A most active inducer of such arrest was shown to be 4-desacetyl leurocristine C-3 N-methylcarboxamide sulfate which was effective at doses on the order of $10^{-6}$ μg/ml. Other compounds of this invention induce metaphase arrest.

In addition, the compounds of this invention have been shown to be active against transplanted mouse tumors in vivo. For example, 4-desacetyl VLB C-3 carboxamide sulfate, 4-desacetyl VLB C-3 N-methylcarboxamide sulfate, VLB C-3 carboxamide sulfate, VLB C-3 N-methylcarboxamide sulfate, 4-desacetyl VLB C-3 N-(2-hydroxyethyl) carboxamide sulfate, 4-desacetyl VLB C-3 N,N-dimethylcarboxamide sulfate, 4-desacetyl leurosidine C-3 amide sulfate, 4-desacetyl VLB C-3 N-benzylcarboxamide sulfate and 4-desacetyl VLB C-3 carboxhydrazide, as well as other compounds coming within the scope of the above formula, demonstrate such activity. Of particular interest, however, is the activity of the compounds of this invention, especially the 4-desacetyl VLB C-3 carboxamide sulfate, and its N-alkyl, N-mercaptoalkyl the corresponding disulfides, and N-hydroxyalkyl derivatives, against Ridgeway osteogenic sarcoma (ROS) and Gardner lymphosarcoma (GLS). In demonstrating activity of the drugs of this invention against these and other tumors, a protocol was used which involved the administration of the drug, usually by the intraperitoneal route, at a given dose level for 7–10 days after innoculation with the tumor.

The following table—Table 1—gives the results of several experiments in which mice bearing transplanted tumors were treated successfully with a compound of this invention. In the table, column 1 gives the name of the compound; column 2, the transplanted tumor; column 3, the dose level or dose level range and the number of days the dosage was administered; and column 4, the percent inhibition of tumor growth/or percent prolongation of survival time, e.g, B16 and P388. (ROS is an abbreviation for Ridgeway osteogenic sarcoma; GlS for Gardner lymphosarcoma; and CA 755 is an adenocarcinoma; C3H mammary carcinoma and P1534 (J) leukemia.

Table 1

| Compound | Tumor | mg/kg. × days | Percent Inhibition |
| --- | --- | --- | --- |
| 4-Desacetyl VLB C-3 N-methylcarboxamide sulfate | C₃H mammary | 0.25–0.3 × 9 | 35–49 |
| | ROS | 0.15–0.3 × 10 | 48–100 |
| | B-16 | 0.216–0.6 × 9 | 25–100 |
| | B-16 | 0.6–1.67 × 3 | 46–100 (100% indefinite survivors) |
| | GLS | 0.5–0.4 × 8 | 60–100 |
| | P1534 (J) (S.C.) | 0.25 × 10 | 89 |
| VLB C-3 carboxamide sulfate | ROS | 0.1–0.5 × 10 | 23–84 |
| | GLS | 0.5–0.8 × 8 | 47–100 |
| 4-Desacetyl leurocristine C-3 N-methylcarboxamide sulfate | C₃H mammary | 1.0 × 9 | 36 |
| | CA755 | 1.0 × 9 | 76 |
| | GLS | 0.3 1.0 × 8 | 57–100 |
| | ROS | 0.1–1.0 × 10 | 39–100 |
| 4-Desacetyl VLB C-3 carboxamide sulfate | GLS | 0.15–1.0 × 10 | 79–100 |
| | ROS | 0.15–0.4 × 10 | 49–100 |
| | P1534 (J) (S.C.) | 0.2–0.25 × 10 | 36–37 |
| 4-Desacetyl VLB C-3 N-ethylcarboxamide sulfate | GLS | 0.2 × 7 | 90 |
| | ROS | 0.1–0.4 × 7–10 | 53–100 |
| 4-Desacetyl VLB C-3 N-benzylcarboxamide sulfate | ROS | 0.3 × 10 | 100 |
| | GLS | 3 × 9 | 29 |
| VLB C-3 N-methylcarboxamide sulfate | GLS | 0.1–0.25 × 8 | 38–100 |
| | ROS | 0.1–0.3 × 10 | 57–100 |
| | P1534 (J) (S.C.) | 0.2 × 9 | 60 |
| 4-Desacetyl VLB C-3 carboxhydrazide | ROS | 0.1–0.3 × 8–10 | 49–100 |
| | GLS | 0.2–0.6 × 7–10 | 73–100 |
| 4-Desacetyl VLB C-3 N-2-hydroxyethylcarboxamide sulfate | ROS | 0.05–0.4 × 10 | 100 |
| | GLS | 0.0125–0.4 × 7–10 | 22–100 |
| | P1534 (J) (S.C.) | 0.05–0.6 × 9 | 31–89 |
| | B1 6 | 1.5–3.0 × 10 | 21–26 |
| | | 0.6–1.67 × 3 (every 4th day) | 48–75 |
| | | 0.2–6 –0.6 × 9 | 55–91 |
| 4-Desacetyl VLB C-3 N,N-dimethylcarboxamide sulfate | ROS | 0.4 × 10 | 53 |
| | GLS | 0.15 × 8 | 69 |
| | | 0.6 × 9 | 77 |
| 4-Desacetyl VLB C-3 N-cyanomethylcarboxamide sulfate | ROS | 0.3 × 10 | 85 |
| | GLS | 0.15–0.2 × 9 | 85–96 |
| 4-Desacetyl VLB C-3 N-2-butyroxyethylcarboxamide sulfate | ROS | 0.2 × 10 | 100 |
| | GLS | 0.1–0.2 × 10 | 72–100 |
| 4-Desacetyl VLB C-4 N-2, 3-di- | ROS | 0.2–0.4 × 10 | 42–100 |

Table 1-continued

| Compound | Tumor | mg/kg. × days | Percent Inhibition |
|---|---|---|---|
| hydroxypropylcarboxamide | GLS | 0.2–0.4 × 7 | 37–56 |
| 4-Desacetoxy VLB C-3 N-2-hydroxyethylcarboxamide sulfate | ROS | 0.5 × 10 | 44 |
|  | GLS | 0.75–1.5 × 6 | 51–100 |
| 4-Desacetyl VLB N-pyrrolidinylcarboxamide sulfate | ROS | 0.2 × 10 | 54 |
| 4-Desacetyl VLB C-3 N-3-hydroxypropylcarboxamide sulfate | GLS | 0.5–0.6 × 7-8 | 41–100 |
|  | ROS | 0.05–0.4 × 10 | 46–100 |
|  | P1534 (J) (S.C.) | 0.2–0.6 × 9 | 85–90 |
| 4-Desacetyl VLB C-3 N-cyclohexylcarboxamide | GLS | 0.4 × 8 | 33 |
|  | ROS | 0.2–0.4 × 10 | 48–63 |
| 4-Desacetyl VLB C-3 N-n-hexylcarboxamide sulfate | ROS | 0.2 × 10 | 34 |
| 4-Desacetyl VLB C-3 N-2-cyanoethylcarboxamide sulfate | GLS | 0.1–0.4 × 9 | 73–100 |
| 4-Desacetyl VLB C-3 N-isopropylcarboxamide | GLS | 0.15–0.2 × 9 | 63–70 |
| 4-Desacetyl VCR C-3 N-methylcarboxamide | GLS | 0.5 1.0 × 9 | 38–63 |
|  | P-1534 (J) (S.C.) | 0.2 × 9 | 60 |
| 4-Desacetyl VCR C-3 C-3 N-isopropylcarboxamide | GLS | 1.0 × 9 | 56 |
| 4-Desacetyl VCR C-3 N-2-hydroxyethylcarboxamide | GLS | 1.5 × 10 | 37 |
|  | ROS | 0.75 × 10 | 85 |
| VCR C-3 carboxamide sulfate | ROS | 0.5 × 10 | 49 |
| Pseudo VLB C-3 N-2-hydroxyethylcarboxamide sulfate | GLS | 0.5 × 7 | 35 |
| 4-Desacetyl Deoxy VLB "B" C-3 carboxhydrazide | GLS | 0.6 × 7 | 77 |
| 4-Desacetyl VLB C-3 N-2-acetoxyethylcarboxamide sulfate | ROS | 0.2 × 10 | 100 |
|  | GLS | 0.05–0.2 × 10 | 37–100 |
| 4-Desacetyl VCR C-3 carboxamide sulfate | GLS | 0.2–1.0 × 7 | 36–75 |
|  | ROS | 1.0 × 10 | 39 |
| 4-Desacetyl VLB C-3 N-2-dimethoxyethylcarboxamide sulfate | GLS | 0.1–0.2 × 7 | 83–100 |
|  | P388 | 0.05 × 10 | 40 |
| 4-Desacetyl VLB C-3 N-2-acetaldehydecarboxamide sulfate | P388 | 0.4 × 10 | 48 |
|  | GLS | 0.1–0.4 × 7-9 | 84–100 |
| 4-Desacetyl VLB C-3 N-2-acrylyloxyethylcarboxamide sulfate | P388 | 0.4 × 10 | 48 |
|  | GLS | 0.05–0.4 × 7-10 | 53–100 |
| bis-[-(4-desacetyl VLB C-3 carboxamido)ethyl]disulfide disulfate | GLS | 0.2–0.4 × 7-9 | 100 |
|  | B16 | 0.8–1.5 × 3 | 16–65 |
| 4-Desacetyl VLB C-3 N-2-stearoyloxyethylcarboxamide sulfate | GLS | 0.2–0.4 × 7-9 | 87–100 |
| 4-Desacetyl VLB C-3 N-2-methoxyethylcarboxamide sulfate | B16 | 0.75 × 10 | indefinite survivors |
| VLB C-3 N-2-acetylamino ethylcarboxamide sulfate | GLS | 0.25–0.5 × 10 | 74–100 (Day 7) |
| 4-Desacetyl VLB C-3 N-2-acetylaminoethylcarboxamide sulfate | GLS | 0.125–0.5 × 10 | 92–100 (Day 7) |
| 4-Desacetyl VLB C-3 N-2-aminoethylcarboxamide sulfate | GLS | 0.25–0.5 × 10 | 33–36 (Day 7) |
| 4-Desacetyl VLB C-3 N-2-aminoethylcarboxamide sulfate | GLS | 0.25–0.5 × 10 | 33–36 (Day 7) |
| 4-Desacetyl VLB C-3 N-(2-mercaptoethyl) carboxamide sulfate | GLS | 0.4 × 7 | 62 |
|  |  | 0.3 × 7 | 51 |
|  |  | 0.2 × 7 | 29 |
| 4-Desacetyl VLB C-3 N-allyl-carboxamide sulfate | GLS | 0.4 × 7 | Toxic |
|  |  | 0.2 × 7 | 80 |
| 4-Desacetyl VLB C-3 N-propargylcarboxamide sulfate | GLS | 0.4 × 7 | Toxic |
|  |  | 0.2 × 7 | 86 |
|  |  | 0.1 × 7 | 54 |
| 4-Desacetyl VLB C-3 N-(3,4-dihydroxyphenylethyl)carboxamide sulfate | GLS | 0.4 × 7 | 36 |
|  |  | 0.2 × 7 | 16 |
|  |  | 0.1 × 7 | 10 |
| 4-Desacetyl VLB C-N-4-hydroxyphenylethyl)carboxamide sulfate | GLS | 0.4 × 7 | 29 |
|  |  | 0.2 × 7 | 21 |
|  |  | 0.2 × 7 | 19 |

Indefinite survivors were found with many of the above regimens.

The compounds of this invention, as with the marketed drugs leurocristine and VLB, become toxic to mice at doses above those at which they produce 100 percent inhibition of the transplanted tumor. In addition, for reasons that are not well understood, all drugs in a given test including control drugs may show toxicity at dose levels where they ordinarily give tumor inhibition without toxicity. Thus, the results set forth in Table 1 are of typical experiments where the control drugs give expected results and are not an average of all runs.

The compounds of this invention are also active against other transplanted tumors. For example, with Mecca lymphosarcoma, parenteral injection of 0.25 mg./kg. for 9 days of VLB C-3 N-methylcarboxamide sulfate gave a 54 percent inhibition of growth and of VLB C-3 amide, a 28 percent inhibition. At the same dose levels, VLB itself was completely inactive. Against L5178Y lymphocytic leukemia, VLB C-3 carboxamide sulfate at a dose level of 0.25 mg./kg. for ten days in an experiment using five mice gave three indefinite survivors; the life span of the two diseased mice in this experiment was prolonged by 26 percent over that of the control mice. In the same experiment, VLB gave a 36 percent prolongation but with no indefinite survivors and rated only a minimal effectiveness rating.

In addition, two compounds coming within the scope of Formula I have been tested against Freund leukemia virus. The results of this testing are set forth in the accompanying table, Table 2, and were obtained by testing 4-desacetyl VLB C-3 amide sulfate and VLB C-3 amide sulfate in a standard Freund leukemia virus assay. Results from testing VLB sulfate and 4-desacetyl VLB sulfate are included for purposes of comparison.

TABLE 2

| | FREUND LEUKEMIA VIRUS ASSAY | | | | | |
|---|---|---|---|---|---|---|
| Compound Name | mg./kg. | Avg. Wt. Gain (gm) | S/N | Avg. Spleen Wt. (mg) | Percent Inhibition | Hematocrit |
| Infected Control | 0.0 | +0.925 ±.924* | 40/40 | 1116. ±688* | — | 62.0 ±3.8* |
| 4-Desacetyl VLB C-3 carboxamide sulfate | 0.1 | +1.5 | 10/10 | 503 | 59.4 | 43.2 |
| | 0.2 | +1.1 | 10/10 | 327 | 76.5 | 43.2 |
| | 0.3 | +2.3 | 10/10 | 237 | 85.2 | 36.6 |
| | 0.4 | +1.5 | 6/10 | 173 | 91.5 | 37.0 |
| VLB Sulfate | 0.1 | −0.9 | 10/10 | 971 | 14.1 | 62.6 |
| | 0.2 | +1.0 | 10/10 | 694 | 40.9 | 52.7 |
| | 0.3 | +1.2 | 10/10 | 330 | 76.2 | 42.9 |
| | 0.4 | +0.3 | 10/10 | 209 | 88.0 | 41.6 |
| VLB C-3 Carboxamide Sulfate | 0.1 | +2.2 | 10/10 | 720 | 38.4 | 48.1 |
| | 0.2 | +2.9 | 10/10 | 290 | 80.1 | 44.1 |
| | 0.3 | +3.0 | 10/10 | 246 | 84.4 | 41.6 |
| | 0.4 | +2.0 | 10/10 | 201 | 88.7 | 38.2 |
| 4-Desacetyl VLB Sulfate | 0.1 | +2.4 | 10/10 | 1115 | 0.0 | 57.9 |
| | 0.2 | +1.5 | 10/10 | 383 | 71.0 | 41.0 |
| | 0.3 | −0.6 | 10/10 | 129 | 95.7 | 42.3 |
| | 0.4 | −1.85 | 4/10 | 054 | 103.0 | 43.0 |

*Confidence intervals determined by $t_1$ test, $\alpha = .01$

As would be expected, the novel amides and hydrazides of this invention differ in their anti-tumor spectrum from VLB, leurocristine and leurosine, as well as from the C-4 N,N-dialkylglycyl esters of VLB in the same way that the anti-tumor spectra of those compounds differ among themselves, some being more effective against certain tumors or classes of tumors and less effective against others. However, in utilizing a compound of this invention clinically, the clinical physician would administer them initially by the same route in the same vehicle and against the same types of tumors as for clinical use of leurocristine and VLB. Differences in dosage level would, of course, be based on relative activity between leurocristine and the new drug in the same experimental tumor in mice. The amides of this invention apparently show decreased neurotoxicity compared with leurocristine.

In utilizing the novel amides and hydrazides of this invention as anti-neoplastic agents, either the parenteral or oral route of administration may be employed. For oral dosage, a suitable quantity of a pharmaceutically-acceptable salt of a base according to Formulas I–IV formed with a non-toxic acid is mixed with starch or other excipient and the mixture placed in telescoping gelatin capsules each containing from 7.5–50 mg. of active ingredients. Similarly, the anti-neoplastically active salt can be mixed with starch, a binder, and a lubricant and the mixture compressed into tablets each containing from the 7.5–50 mgs. of salt. The tablets may be scored if lower or divided dosages are to be used. For this purpose, isotonic solutions are employed containing 1–10 mg./ml. of a salt of an indoledihydroindole amide of formula I–IV. The compounds are administered at the rate of from 0.01 to 1 mg./kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range 0.1 to 10 mg./meter squared of mammalian body surface every 7 or 14 days.

In addition, one of the compounds of this invention, 4-desacetyl VLB C-3 carboxamide (referred generically as vindesine) is presently undergoing a clinical trial in humans against selected malignancies. The clinical trial is being carried out in accordance with a procedure suggested by S. K. Carter in a section headed "Study Design Principles for the Clinical Evaluation of New Drugs as Developed by the Chemotherapy Programme of the National Cancer Institute" to be found on pages 242–289 of a recent book "The Design of Clinical Trials in Cancer Therapy" edited by Maurice Staquet (Futura Publishing Co., New York, 1973). The above section refers to 10 "signal" tumors which have been designated by the National Cancer Institute as those tumors against which clinical trial candidates should be screened. These include adenocarcinoma of the breast, adenocarcinoma of the colon, bronchogenic carcinoma, adenocarcinoma of the pancreas, ovarian cancer, malignant melanoma, acute myelocytic leukemia, acute lymphocytic leukemia, lymphomatous disease and malignant glyoma. Vindesine has been subjected to pharmacokinetic studies by Nelson, et al. and by Owellen, et al. *Proceedings American Association for Cancer Research*, Abstracts Nos. 118 and 406 (May 4–8, 1976). In these studies, vindesine was administered to patients with advanced cancer at a dose level of 2–3 mg./square meter of body surface by the intravenous route. A radioimmune assay employing antibodies to an antigen prepared by reacting 4-desacetyl VLB C-3 carboxazide with protein was employed to determine blood levels. The above dose levels were on a weekly basis and during this study, divided dosages of 1 to 1½ mg. per square meter of body surface were given on a semi-weekly basis. These pharmacokinetic studies demonstrated that doses of that magnitude did not show undue signs of toxicity. Clinical trial was then initiated by two different groups which reported their results at the same meeting (*iBiD* Abstracts No. 510 and 694). In one of these studies, dosages of vindesine by the intravenous route varying from 2 to 12.5 mg. over each 7 or 14 days produced a number of physiological effects. It is believed that dosages of 4 mg./square meter or large would cause undue toxicity. At the lower dosage rates, two out of nine patients with acute leukemia achieved partial remissions and one out of four patients with squamous cell carcinoma and one out of four with renal cell carcinoma achieved some response. No response was seen in a number of other malignancies. In the second study, vindesine was given at doses ranging from 0.5–6 mg/square meter to 42 adults and 9 children. None of the children developed neurotoxicity. Minor response was seen in a variety of tumors. In further studies carried out by Richard W. Dyke, M.D. of the Lilly Laboratory for Clinical Research, Indianapolis, Indiana, Administration of vindesine in the same dosage range was able to maintain an adult with an acute leukemia in remission (produced by other agents) for a 3–4 month period. An initial (partial) response was also seen in a malignant melanoma after 8 doses. Both of these patients are still being carried on vindesine. It is expected that further clinical results will be forthcoming from this trial of vindesine in human malignancies.

We claim:

1. A compound of the formula

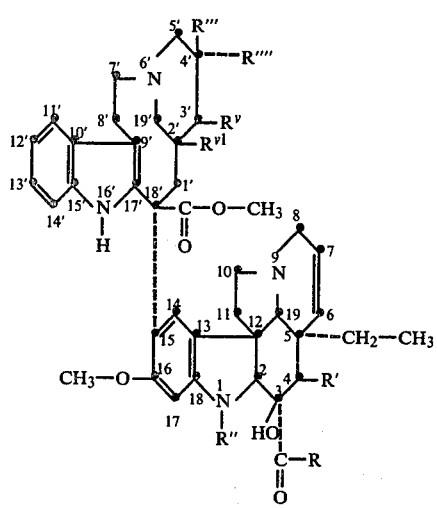

I wherein R is $NH_2$, $NH-NH_2$, $N(CH_3)_2$, $N_3$, $NH-CH_2-Y$ wherein Y is H, CN, CHO, $CH(O-C_1-C_3-alkyl)_2$, $NH-C_2-C_6$-alkyl-X, $NH-C_2-C_6$-alkyl-$(OH)_{1-3}$, $NH-(CH_2)_n-OAc$, $NH-(CH_2)_n-OCH_3$, n is 2 or 3, X is SY', $NH_2$, $NHCH_3$, $N(CH_3)_2$, NHAc, CN, H, phenyl, or COOH, Y' is H, or $C_1-C_3$-alkyl and Ac is $C_1-C_{17}$-alkyl-CO or $C_2-C_7$-alkenyl-CO, pyrrolidinyl or $NH-C_3-C_8$-cycloalkyl; R' is H, OH, O—$(C_1-C_3)$-alkanoyl or O-chloro-$(C_1-C_3)$-alkanoyl, R" is hydrogen, methyl or formyl, one of R''' and R'''' is hydrogen or hydroxyl and the other is ethyl, and $R^v$ and $R^{vI}$ are hydrogen or hydroxyl, with the proviso that, when either R''' or R'''' is hydrogen, $R^v$ and $R^{vI}$ must also be hydrogen and pharmaceutically-acceptable salts thereof.

2. A sulfate salt of a compound according to claim 1.

3. A compound according to claim 1 in which R is $NH_2$, R' is OH, R" is methyl, R''' is hydroxyl, R'''' is ethyl, and $R^v$ and $R^{vI}$ are H, said compound being 4-desacetyl VLB C-3 carboxamide.

4. The sulfate salt of the compound of claim 3.

5. A compound according to claim 1 in which R is $NH-CH_3$, R' is acetoxy, R" is methyl, R''' is hydroxyl, R'''' is ethyl, and $R^v$ and $R^{vI}$ are H, said compound being VLB C-3 N-methylcarboxamide.

6. The sulfate salt of the compound of claim 5.

7. A compound according to claim 1 in which R is $NH-CH_3$, R' and R''' are hydroxyl, R" is formyl, R'''' is ethyl and $R^v$ and $R^{vI}$ are H, said compound being 4-desacetyl leurocristine C-3 N-methylcarboxamide.

8. The sulfate salt of the compound of claim 7.

9. A compound according to claim 1 in which R is $NH-NH_2$, R' and R''' are hydroxyl, R" is methyl, R'''' is ethyl, and $R^v$ and $R^{vI}$ are H, said compound being 4-desacetyl VLB C-3 carboxhydrazide.

10. A compound according to claim 1 in which R is $N_3$, R' and R''' are hydroxyl, R" is methyl, R'''' is ethyl, and $R^v$ and $R^{vI}$ are H, said compound being 4-desacetyl VLB C-3 carboxazide.

11. A compound according to claim 1 in which R is $NH-C_2H_4OH$, R' and R''' are hydroxyl, R" is methyl, R'''' is ethyl, and $R^v$ and $R^{vI}$ are H, said compound being 4-desacetyl VLB C-3 N-(2-hydroxyethyl)carboxamide.

12. A compound according to claim 1 in which R is $NH-C_2H_4OH$, R" is methyl, R''' is OH, R'''' is ethyl, and R', $R^v$ and $R^{vI}$ are H, said compound being 4-desacetoxy VLB C-3 N-(2-hydroxyethyl)carboxamide.

13. The sulfate salt of the compound of claim 11.

14. A compound according to claim 1 in which R is $NHCH_3$, R' and R''' are OH, R" is $CH_3$, R'''' is $C_2H_5$ and $R^v$ and $R^{vI}$ and H, said compound being 4-desacetyl VLB C-3 N-methylcarboxamide.

15. A compound according to claim 1 in which R is $(NH-CH_2-CH_2-S-)_2$ R' and R''' are OH, R" is $CH_3$, R'''' is $C_2H_5$ and $R^v$ and $R^{vI}$ are H, said compound being bis-[β-(4-desacetyl VLB C-3 carboxamido)ethyl]-disulfide.

16. The sulfate salt of the compound of claim 15.

17. A compound of the formula

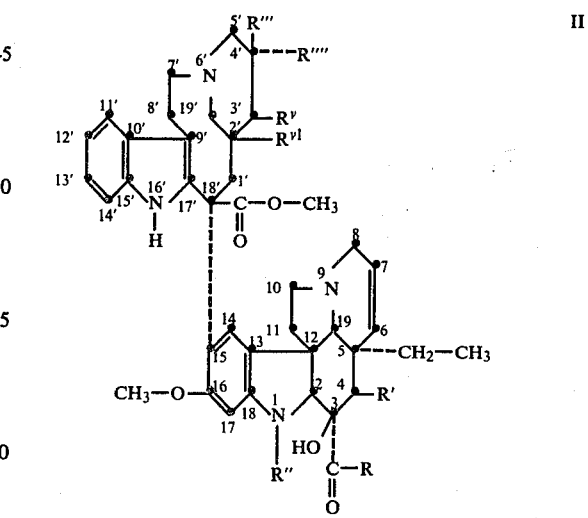

II wherein R is $NH_2$, $NH-NH_2$, $NHCH_3$, $N(CH_3)_2$, pyrrolidinyl, NH-alk-X, $NH-(C_3-C_8)$-cycloalk, NH-alk-Am, NH-alk-$(OH)_{1-3}$, or $N_3$; wherein alk is $(C_2-C_6)$ alkyl, Am is $NH_2$, $NHCH_3$ or $N(CH_3)_2$ and X is hydrogen, cyano or phenyl; wherein R' is H, OH, O—(C-

1-C3)-alkanoyl or O-chloro-(C1-C3)-alkanoyl; wherein R" is hydrogen, methyl or formyl; and wherein one of R'" and R"" is hydrogen or hydroxyl and the other is ethyl, and $R^v$ and $R^{vi}$ are H or OH with the proviso that, if one of R'" or R"" is hydrogen, $R^v$ and $R^{vi}$ must also be hydrogen and pharmaceutically-acceptable salts thereof.

18. A sulfate salt of a compound according to claim 17 in which R is NH2 or N—(C1—C3)-alkyl and R' and R" are defined as hereinabove.

19. A compound of the formula

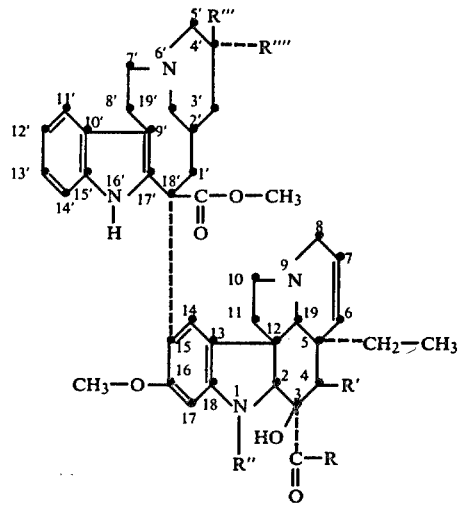

III wherein R is NH2, NH—NH2, N(CH3)2, NH-alk-X, NH(C3-C8)-cycloalk, NH-alk-Am, NH-alk-(OH)1-3, or N3; wherein alk is (C1-C6) alkyl, Am is NH2, NHCH3 or N(CH3)2 and X is hydrogen, cyano, or phenyl, wherein R' is OH, O—(C1-C3)-alkanoyl or O-chloro-(C1-C3)-alkanoyl; wherein R" is hydrogen, methyl, formyl or (C1-C3)-alkanoyl; and wherein one of R'" and R"" is hydroxyl and the other is ethyl and pharmaceutically-acceptable salts thereof.

20. A compound of the formula

IV wherein
R is NH2; NH—C1-C3-alkyl or NH—NH2,
R' is OH, O—C1-C3 alkanoyl or O-Chloro-C1-C3 alkanoyl and R" is H, methyl or formyl and pharmaceutically-acceptable salts thereof.

21. A sulfate salt of a compound according to claim 20.

22. A compound of the formula

I wherein

R is CH2—CH=CH2, CH2—C≡CH, or wherein m is 0 or 1;

R' is H, OH, O—(C1-C3)-alkanoyl or O-chloro-(C1-C3)-alkanoyl, R" is hydrogen, (C1-C3)-alkyl or formyl, one of R'" and R"" is hydrogen or hydroxyl and the other is ethyl, and $R^v$ and $R^{vi}$ are hydrogen or hydroxyl, with the proviso that, when either R'" or R"" is hydrogen, $R^v$ and $R^{vi}$ must also be hydrogen and pharmaceutically-acceptable salts thereof.

23. A compound of the formula

Q—NH—(CH2)$_p$—S—S(CH2)$_p$—NH—Q wherein p is 2 or 3 and Q is

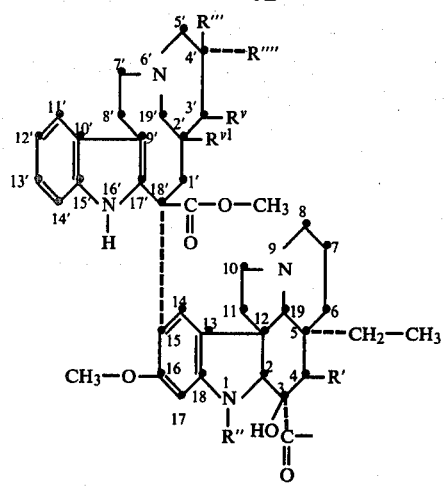
wherein R' is H, OH, O—($C_1$–$C_3$)-alkanoyl or O-chloro-($C_1$–$C_3$)-alkanoyl, R'' is hydrogen, ($C_1$–$C_3$)-alkyl or formyl, one of R''' and R'''' is hydrogen or hydroxyl and the other is ethyl, and $R^v$ and $R^{vI}$ are hydrogen or hydroxyl, with the proviso that, when either R''' or R'''' is hydrogen, $R^v$ and $R^{vI}$ must also be hydrogen and pharmaceutically-acceptable salts thereof.
* * * * *